(12) United States Patent
Akizuki et al.

(10) Patent No.: US 8,437,821 B2
(45) Date of Patent: May 7, 2013

(54) NON-INVASIVE BODY INFORMATION MEASUREMENT APPARATUS

(75) Inventors: Mamiko Akizuki, Ehime (JP); Yasushi Ueda, Ehime (JP); Hiroyoshi Inoshita, Ehime (JP)

(73) Assignee: Panasonic Corporation, Osaka (JP)

( * ) Notice: Subject to any disclaimer, the term of this patent is extended or adjusted under 35 U.S.C. 154(b) by 1158 days.

(21) Appl. No.: 12/349,165

(22) Filed: Jan. 6, 2009

(65) Prior Publication Data
US 2010/0174159 A1   Jul. 8, 2010

(51) Int. Cl.
*A61B 5/00* (2006.01)
(52) U.S. Cl.
USPC .......................... 600/316; 600/322; 600/365
(58) Field of Classification Search .................. 600/316, 600/322, 319, 365, 310, 309
See application file for complete search history.

(56) References Cited

U.S. PATENT DOCUMENTS

| | | | |
|---|---|---|---|
| 4,975,581 A * | 12/1990 | Robinson et al. | 250/339.09 |
| 5,435,309 A * | 7/1995 | Thomas et al. | 600/310 |
| 5,507,288 A * | 4/1996 | Bocker et al. | 600/322 |
| 5,830,132 A * | 11/1998 | Robinson | 600/310 |
| 5,857,462 A * | 1/1999 | Thomas et al. | 600/310 |
| 5,910,109 A * | 6/1999 | Peters et al. | 600/316 |
| 6,040,578 A * | 3/2000 | Malin et al. | 250/339.12 |
| 6,064,896 A * | 5/2000 | Rosenthal | 600/316 |
| 6,309,884 B1 * | 10/2001 | Cooper et al. | 436/14 |
| 6,403,944 B1 | 6/2002 | MacKenzie et al. | |
| 6,558,320 B1 * | 5/2003 | Causey et al. | 600/300 |
| 6,998,247 B2 * | 2/2006 | Monfre et al. | 435/14 |
| 7,183,102 B2 * | 2/2007 | Monfre et al. | 435/287.1 |
| 7,409,239 B2 * | 8/2008 | Chung et al. | 600/316 |
| 2005/0033127 A1 * | 2/2005 | Ciurczak et al. | 600/316 |
| 2005/0113657 A1 * | 5/2005 | Alarcon et al. | 600/342 |
| 2007/0265514 A1 * | 11/2007 | Kiani | 600/365 |
| 2008/0086038 A1 * | 4/2008 | Thornton | 600/310 |

FOREIGN PATENT DOCUMENTS

| | | |
|---|---|---|
| JP | 2001-526557 | 12/2001 |
| WO | 98/38904 | 9/1998 |

* cited by examiner

*Primary Examiner* — Julian Woo
*Assistant Examiner* — Christopher L Templeton
(74) *Attorney, Agent, or Firm* — Wenderoth, Lind & Ponack, L.L.P.

(57) ABSTRACT

A non-invasive body information measurement apparatus, in which a blood glucose level is corrected using a blood glucose level measured with an invasive blood glucose measurement apparatus, wherein in a calibration period, measurement of body information is performed at a plurality of luminous energy levels, a plurality of estimated blood glucose levels are calculated from a plurality of characteristic quantities calculated at the various luminous energy levels and from blood glucose levels measured with an invasive blood glucose measurement apparatus, and at the end of the calibration period, the blood glucose levels measured with the invasive blood glucose measurement apparatus are compared with a plurality of estimated blood glucose levels, and in a normal measurement period a light source is controlled so that measurement is performed at a luminous energy level corresponding to the estimated blood glucose level that satisfies the targeted accuracy.

9 Claims, 9 Drawing Sheets

NON-INVASIVE BODY INFORMATION MEASUREMENT APPARATUS

BACKGROUND OF THE INVENTION

1. Field of the Invention

The present invention relates to a non-invasive body information measurement apparatus with which body information can be measured without resorting to invasive procedures, and in particular relates to a non-invasive body information measurement apparatus which can select a luminous energy level in a normal measurement period on the basis of a blood glucose level non-invasively measured during a calibration period.

2. Description of the Related Art

The number of patients with diabetes, which is a typical lifestyle disease, is on the rise around the world. Diabetic patients must constantly control their blood glucose in order to improve their quality of life by suppressing the complications associated with diabetes. To this end, these patients have to measure their blood glucose level on a regular basis every day under the supervision of a physician.

A common way to measure blood glucose is to use an invasive type of blood glucose measurement apparatus, which pricks the finger of the patient, collects a blood sample, and measures the blood glucose level. With this invasive blood glucose measurement apparatus, however, pricking the finger to collect a blood sample involves pain and inconvenience, entails the risk of infection, and so forth, and therefore a non-invasive blood glucose measurement apparatus has been proposed that does not require the collection of a blood sample.

As an example of this non-invasive blood glucose measurement apparatus, a "system for measuring a biological parameter by means of photoacoustic interaction" that makes use of a photoacoustic effect has been proposed (see Patent Document 1 (WO 98/38904), for example).

With this "system for measuring a biological parameter by means of photoacoustic interaction" that makes use of a photoacoustic effect, light of a wavelength that is absorbed by glucose is emitted from the biological measurement system and directed at a part of the body, such as a fingertip, and the emitted light is converged onto a relatively small focal area within the body. Also, the converged light is generally absorbed by glucose, and is converted into kinetic energy in tissue within the focal region and the adjacent region.

The kinetic energy converted in the tissue raises the temperature and pressure of the absorbing tissue region, and generates an acoustic wave. This acoustic wave will hereinafter be referred to as a "photoacoustic wave signal." The photoacoustic wave signal radiates out from the absorbing tissue region and is detected by an acoustic sensor provided to the biological measurement system. This acoustic sensor is installed so as to be in contact with the body surface. The intensity of the photoacoustic wave signal is a function of the amount of glucose in the absorbing tissue region, and the intensity measured by the sensor is used to determine the blood glucose level.

SUMMARY OF THE INVENTION

Nevertheless, with the technology discussed in the above-mentioned Patent Document 1, the photoacoustic wave obtained from the body is extremely weak, and the output of a laser that will give a signal that allows a characteristic quantity to be estimated from a change in this weak signal has been used regardless of the thickness of a vein, the blood glucose concentration, or other aspects of the user's body condition. Consequently, a high-output laser is used even for users with whom a satisfactory signal could be obtained at a lower output, which means that power consumption ends up being higher, which is a drawback in that it is unsuited to portable devices.

Also, with the technology discussed in the above-mentioned Patent Document 1, measurement is carried out a number of times and the series of measurement results are averaged in order to minimize the effects of noise and body movements. Therefore, the problem was not only power consumption, but also that measurement took longer.

It is an object of the present invention to provide a non-invasive body information measurement apparatus that solves the problems encountered in the past, and that selects the luminous energy level of the laser according to the user's body condition, thereby reducing power consumption and measurement time.

To solve the above-mentioned problems encountered in the past, the non-invasive body information measurement apparatus pertaining to the present invention is one in which a measured blood glucose level is corrected using a blood glucose level measured with an invasive blood glucose measurement apparatus, said non-invasive body information measurement apparatus comprising a light source, a body information sensor, a characteristic quantity detector, a blood glucose level estimator, and a controller. The body information sensor measures body information. The characteristic quantity detector analyzes the body information measured by the body information sensor and calculates a characteristic quantity for the body information. The blood glucose level estimator finds an estimated blood glucose level from the characteristic quantity calculated by the characteristic quantity detector and the blood glucose level measured by the invasive blood glucose measurement apparatus. The controller, during a calibration period, performs measurement of the body information at a plurality of luminous energy levels and calculates a plurality of the estimated blood glucose levels from the plurality of characteristic quantities calculated at the various luminous energy levels and the blood glucose levels measured by the invasive blood glucose measurement apparatus, and at the end of the calibration period compares the plurality of estimated blood glucose levels with the blood glucose levels measured by the invasive blood glucose measurement apparatus, and during the normal measurement period controls the light source so that measurement is performed at the luminous energy levels corresponding to the estimated blood glucose levels that satisfy the targeted accuracy.

Further, with this non-invasive body information measurement apparatus, the blood glucose level estimator has a luminous energy level selector that compares the plurality of estimated blood glucose levels with the blood glucose levels measured by the invasive blood glucose measurement apparatus, calculates the average error, and detects the smallest luminous energy level at which the average error is under a preset threshold.

Further, with this non-invasive body information measurement apparatus, the luminous energy level selector has a register that can be written to from the outside, and the luminous energy level selector changes the threshold on the basis of the value of the register.

Further, with this non-invasive body information measurement apparatus, the controller has a luminous energy level modifier that controls the luminous energy level according to a luminous energy level command signal outputted from the blood glucose level estimator.

Further, with this non-invasive body information measurement apparatus, the luminous energy level modifier has a first register group that can be written to from the outside, and the luminous energy level modifier modifies the luminous energy level according to the luminous energy level command signal.

Further, with this non-invasive body information measurement apparatus, the controller has a periodic luminous energy level checker that during the normal measurement period changes the timing at which the light source is turned on in a preset cycle, and outputs the luminous energy level after changing it to a preset value.

Further, with this non-invasive body information measurement apparatus, the periodic luminous energy level checker has a register that can be written to from the outside, and the periodic luminous energy level checker changes the cycle on the basis of the value of the register.

Further, with this non-invasive body information measurement apparatus, the periodic luminous energy level checker has a register that can be written to from the outside, and the periodic luminous energy level checker changes the luminous energy level on the basis of the value of the register.

Further, with this non-invasive body information measurement apparatus, the blood glucose level estimator has a favorable luminous energy level checker that compares the estimated blood glucose level measured at a luminous energy level changed by the periodic luminous energy level checker with the estimated blood glucose level measured at the luminous energy level that was set prior to being changed by the periodic luminous energy level checker, calculates an error, determines whether or not the error is at or below a preset threshold, and, if the error is at or below the preset threshold, outputs to the controller a luminous energy level restoration signal so as to return to the luminous energy level that was set prior to being changed by the periodic luminous energy level checker.

Further, with this non-invasive body information measurement apparatus, the favorable luminous energy level checker has a register that can be written to from the outside, and the favorable luminous energy level checker changes the threshold on the basis of the value of the register.

Also, with the non-invasive body information measurement apparatus pertaining to the present invention, a measured blood glucose level is corrected using a blood glucose level measured with an invasive blood glucose measurement apparatus, said non-invasive body information measurement apparatus comprising a light source, a body information sensor, a characteristic quantity detector, a blood glucose level estimator, and a controller. The body information sensor measures body information. The characteristic quantity detector averages a plurality of pieces of body information repeatedly measured a specific number of times by the body information sensor, analyzes the averaged body information, and calculates a characteristic quantity for the body information. The blood glucose level estimator finds an estimated blood glucose level from the characteristic quantity calculated by the characteristic quantity detector and the blood glucose level measured by the invasive blood glucose measurement apparatus. The controller, during a calibration period, calculates a plurality of the estimated blood glucose levels from the plurality of characteristic quantities calculated from the various pieces of body information repeatedly measured a specific number of times and the blood glucose levels measured by the invasive blood glucose measurement apparatus, and at the end of the calibration period compares the plurality of estimated blood glucose levels with the blood glucose levels measured by the invasive blood glucose measurement apparatus, and during the normal measurement period controls the light source and the characteristic quantity detector so that measurement is performed the number of repetitions corresponding to the estimated blood glucose levels that satisfy the targeted accuracy.

Further, with this non-invasive body information measurement apparatus, the blood glucose level estimator has a repetition count selector that compares the plurality of estimated blood glucose levels with the blood glucose levels measured by the invasive blood glucose measurement apparatus, calculates the average error, and detects the smallest repetition count at which the average error is under a preset threshold.

Further, with this non-invasive body information measurement apparatus, the repetition count selector has a register that can be written to from the outside, and the repetition count selector changes the threshold on the basis of the value of the register.

Further, with this non-invasive body information measurement apparatus, the controller has a repetition count modifier that controls the repetition count according to a repetition count command signal outputted from the blood glucose level estimator.

Further, with this non-invasive body information measurement apparatus, the repetition count modifier has a first register group that can be written to from the outside, and modifies the repetition count according to the repetition count command signal.

Further, with this non-invasive body information measurement apparatus, the controller has a periodic repetition count checker that during the normal measurement period changes the timing at which the light source is turned on in a preset cycle, and outputs the repetition count after changing it to a preset value.

Further, with this non-invasive body information measurement apparatus, the periodic repetition count checker has a register that can be written to from the outside, and the periodic repetition count checker changes the cycle in which the repetition count is changed on the basis of the value of the register.

Further, with this non-invasive body information measurement apparatus, the periodic repetition count checker has a register that can be written to from the outside, and the periodic repetition count checker changes the value of the repetition count on the basis of the value of the register.

Further, with this non-invasive body information measurement apparatus, the blood glucose level estimator has a favorable repetition count checker that compares the estimated blood glucose level measured at a repetition count changed by the periodic repetition count checker with the estimated blood glucose level measured at the repetition count that was set prior to being changed by the periodic repetition count checker, calculates an error, determines whether or not the error is at or below a preset threshold, and, if the error is at or below the preset threshold, outputs to the controller a repetition count restoration signal so as to return to the repetition count that was set prior to being changed by the periodic repetition count checker.

Further, with this non-invasive body information measurement apparatus, the favorable repetition count checker has a register that can be written to from the outside, and the favorable repetition count checker changes the threshold on the basis of the value of the register.

With the non-invasive body information measurement apparatus of the present invention, power consumption is reduced and measurement takes less time, so the continuous measurement time can be improved.

DETAILED DESCRIPTION OF THE PREFERRED EMBODIMENTS

Embodiments of the non-invasive body information measurement apparatus of the present invention will now be described in detail along with the drawings.

Embodiment 1

In Embodiment 1 of the present invention, the non-invasive body information measurement apparatus is assumed to be a non-invasive blood glucose measurement apparatus 101.

Figure 1:
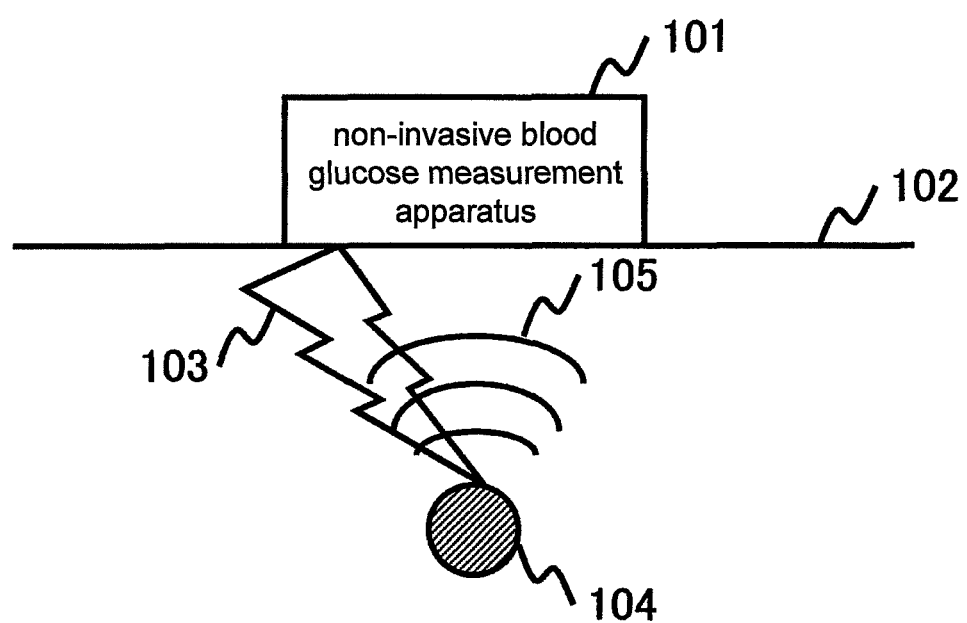
FIG. 1 illustrates the system configuration in Embodiment 1 of the present invention.
Figure 2:
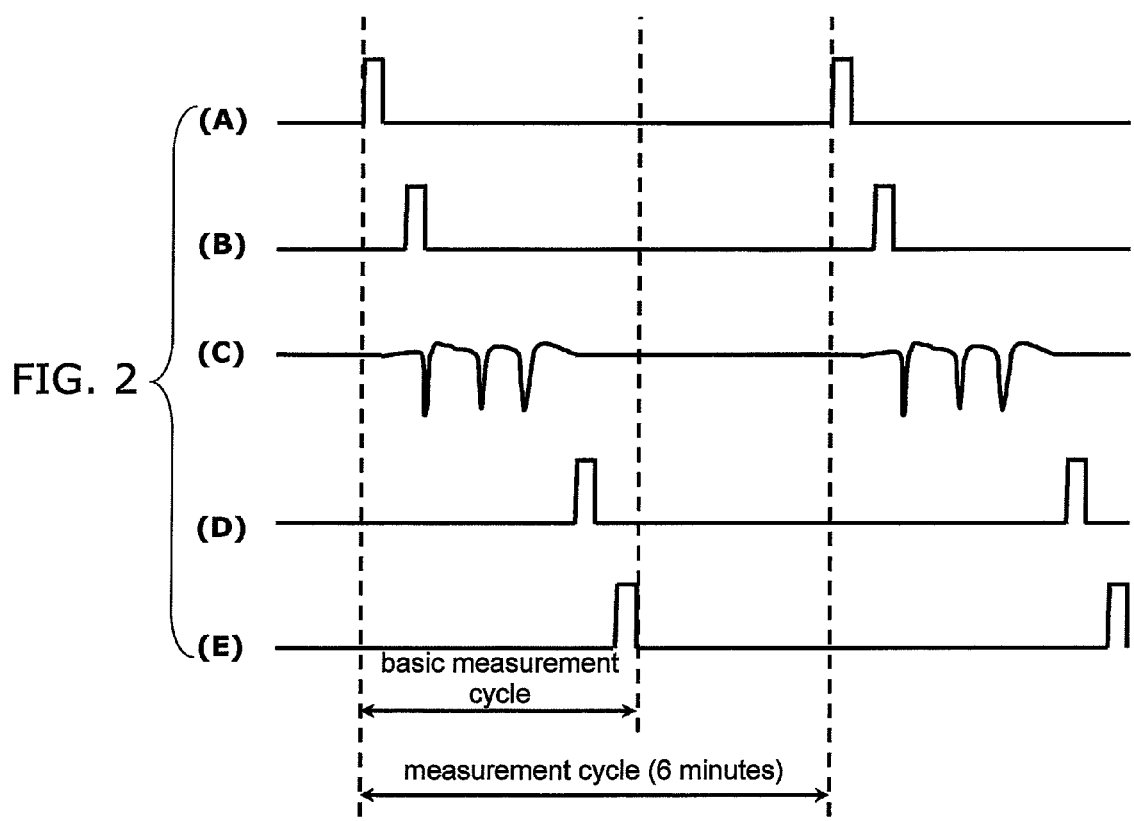
FIG. 2 illustrates the system configuration in Embodiment 1 of the present invention.

FIGS. 1 and 2 illustrate the system configuration in Embodiment 1 of the present invention. In FIG. 1, 101 is a non-invasive blood glucose measurement apparatus, 102 is a body surface, 103 is light, 104 is a vein, and 105 is a photoacoustic wave signal. In FIG. 2, (A) is an actuation signal 83, (B) is the timing 82 at which the light is switched on, (C) is the photoacoustic wave signal 105, (D) is an end signal 84, and (E) is the timing at which an estimated blood glucose level is calculated.

The non-invasive blood glucose measurement apparatus 101 is placed directly on the body surface 102, and the light 103 emitted from the non-invasive blood glucose measurement apparatus 101 is shined on the body. The light 103 propagates through the body and is absorbed by substances in the vein 104 that allow the blood glucose level to be estimated, and the photoacoustic wave signal 105 is produced. The non-invasive blood glucose measurement apparatus 101 detects the photoacoustic wave signal 105 produced by the substances in the vein 104 that allow the blood glucose level to be estimated, and estimates the blood glucose level, which is a characteristic quantity of body information.

Figure 3:
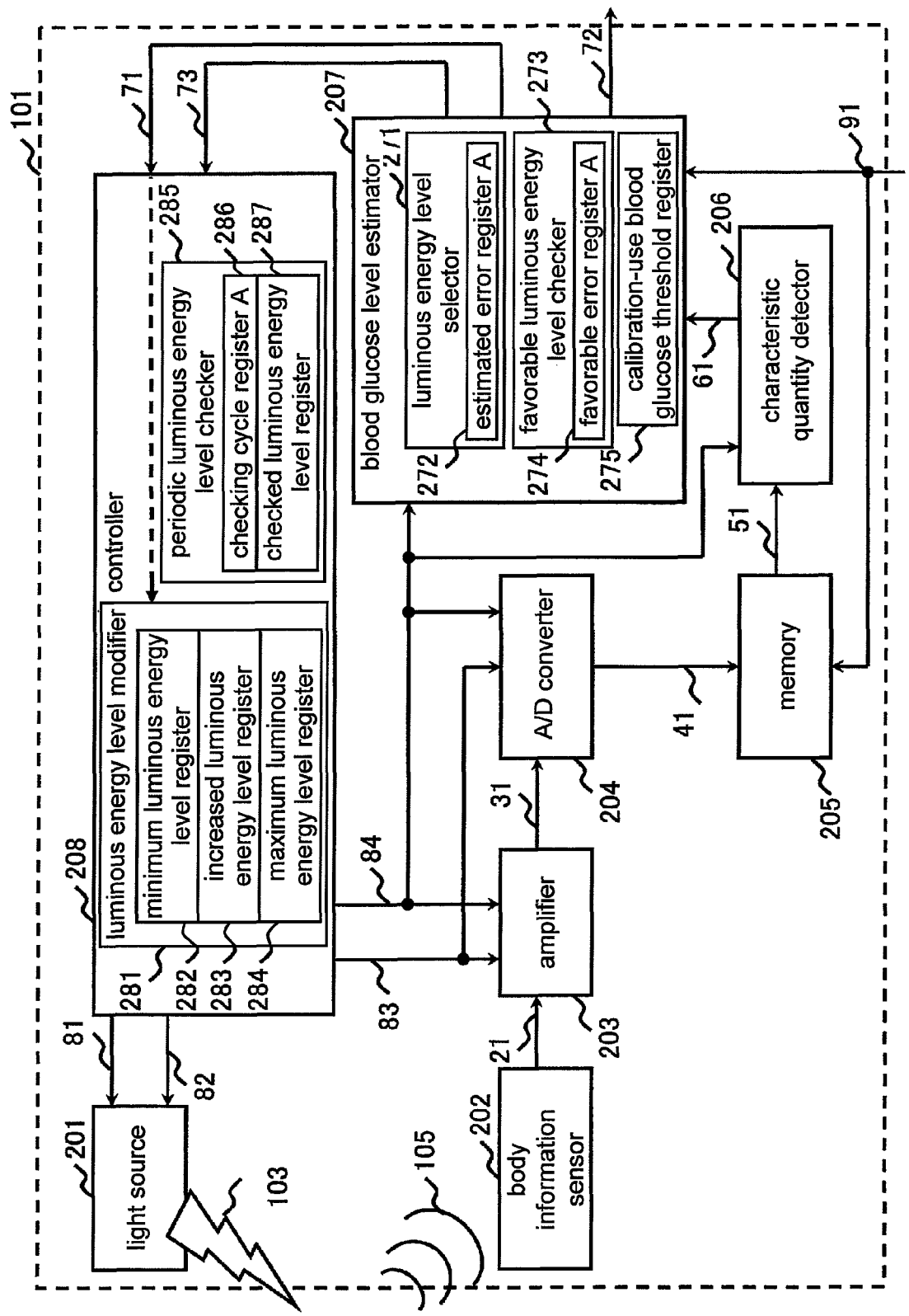
FIG. 3 is a block diagram of the non-invasive blood glucose measurement apparatus in Embodiment 1 of the present invention.

FIG. 3 is a block diagram of the configuration of the non-invasive blood glucose measurement apparatus 101 in Embodiment 1 of the present invention. As shown in FIG. 3, the non-invasive blood glucose measurement apparatus 101 comprises a light source 201, a body information sensor 202, an amplifier 203, an A/D converter 204, a memory 205, a characteristic quantity detector 206, a blood glucose level estimator 207, and a controller 208.

The light source 201 emits the light 103, which has a wavelength that absorbs substances in the vein 104 that allow the blood glucose level to be estimated. One or more light sources 201 are provided.

The controller 208 comprises a luminous energy level modifier 281 and a periodic luminous energy level checker 285, and changes the luminous energy level 81 of the light source 201 according to a luminous energy level command signal 71, controls the timing at which the light source 201 is switched on, and outputs the actuation signal 83 to the amplifier 203 and the A/D converter 204, and the end signal 84 to the amplifier 203, the A/D converter 204, the characteristic quantity detector 206, and the blood glucose level estimator 207.

The luminous energy level modifier 281 outputs to the light source 201 the luminous energy level 81 corresponding to the luminous energy level command signal 71 outputted by the blood glucose level estimator 207.

During the normal measurement period, the periodic luminous energy level checker 285 changes the luminous energy level 81 to a value preset in a checked luminous energy level register 287, at a cycle in which the switch-on timing 82 of the light source 201 has been preset in a checking cycle register A 286.

The body information sensor 202 converts the photoacoustic wave signal 105 into a voltage signal 21. The amplifier 203 detects the voltage signal 21 on the basis of the actuation signal 83 from the controller 208, and produces an amplified signal 31. The A/D converter 204 converts the amplified signal 31 into sampling data 41 on the basis of the actuation signal 83 form the controller 208. The memory 205 is written by the A/D converter 204 in the region where the sampling data 41 is to be stored, and is read by the characteristic quantity detector 206. The characteristic quantity detector 206 analyzes the stored data 51 and calculates a characteristic quantity 61 for body information.

The blood glucose level estimator 207 is made up of a luminous energy level selector 271 and a favorable luminous energy level checker 273, and calculates calibration data when the amount of change in the blood glucose level measured with an invasive blood glucose measurement apparatus (not shown) has reached or exceeded a threshold preset in a calibration-use blood glucose threshold register 275. The blood glucose level estimator 207 also finds an estimated blood glucose level 72 from the characteristic quantity 61 calculated by the characteristic quantity detector 206 and the blood glucose level measured by the invasive blood glucose measurement apparatus, on the basis of the calculated calibration data, and outputs this to the outside.

The luminous energy level selector 271 compares the plurality of estimated blood glucose levels with the blood glucose levels measured by the invasive blood glucose measurement apparatus, calculates the average error, detects the smallest luminous energy level at which the average error is under a threshold preset in an estimated error register A 272, and outputs the luminous energy level command signal 71.

The favorable luminous energy level checker 273 compares the estimated blood glucose level measured at a luminous energy level changed by the periodic luminous energy level checker 285 with the estimated blood glucose level measured at the luminous energy level that was set prior to the change by the periodic luminous energy level checker 285, calculates an error, and determines whether or not the error is at or below a threshold preset in a favorable error register A 274. If the error is at or below the threshold, the favorable luminous energy level checker 273 outputs to the controller 208 a luminous energy level restoration signal 73 so as to return to the luminous energy level that was set prior to being changed by the periodic luminous energy level checker 285.

Figure 4:
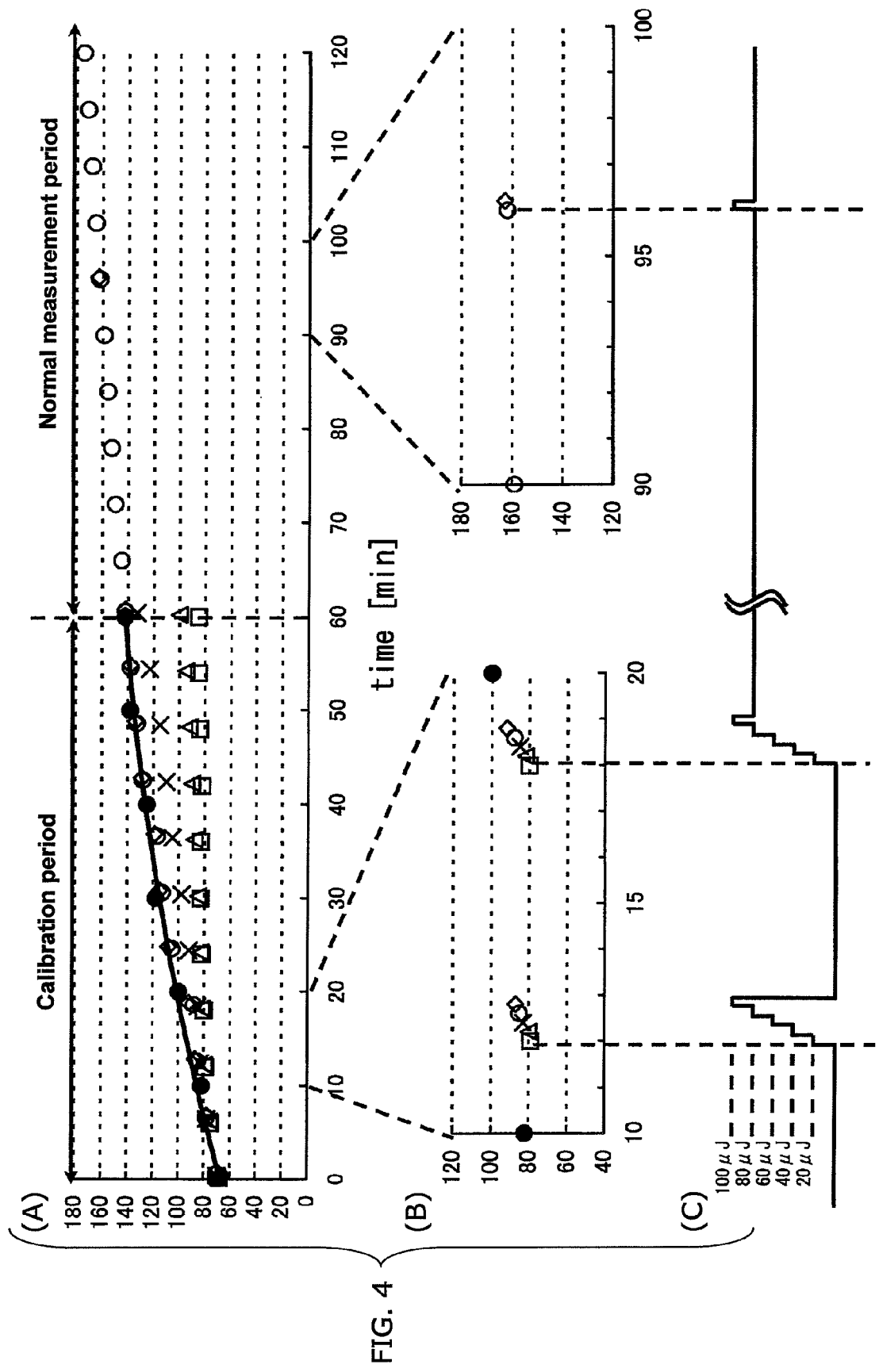
FIG. 4 is a graph in which the estimated blood glucose levels of the non-invasive blood glucose measurement apparatus in Embodiment 1 of the present invention are plotted on a time axis.

FIG. 4 shows the estimated blood glucose level 72 of the non-invasive blood glucose measurement apparatus 101 in Embodiment 1 of the present invention plotted on a time axis. In FIG. 4, (A) is the estimated blood glucose level 72, (B) is an enlarged view of the estimated blood glucose level 72 (at a time of 10 to 20 minutes, and at a time of 90 to 100 minutes), and (C) is the luminous energy level 81.

Figure 5:
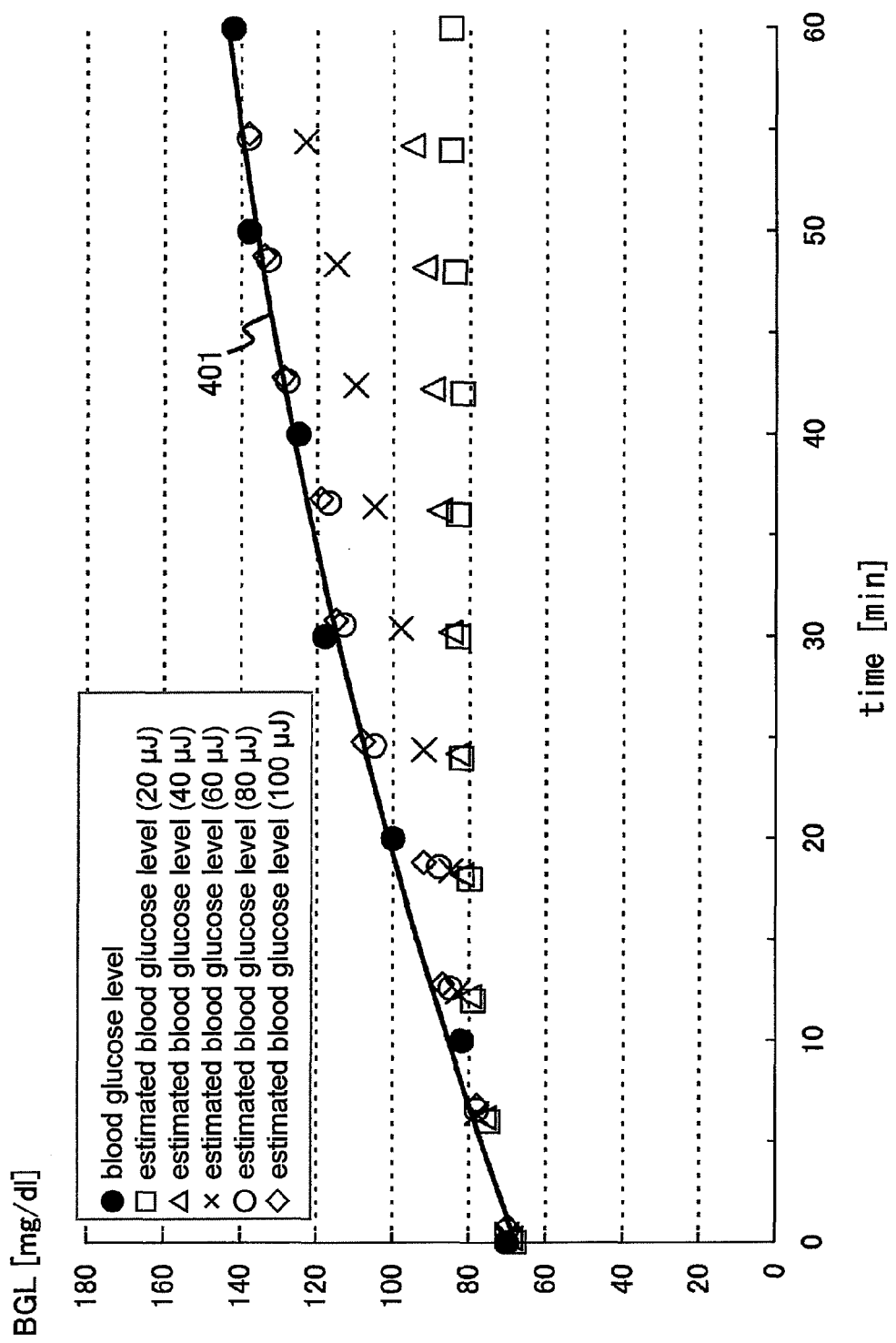
FIG. 5 is an enlarged graph in which the estimated blood glucose levels and the blood glucose levels of the non-invasive blood glucose measurement apparatus and the invasive blood glucose measurement apparatus in Embodiment 1 of the present invention are plotted on the time axis at a time of 0 to 20 minutes.

FIG. 5 is an enlarged graph in which the estimated blood glucose level 72 and the blood glucose level of the non-invasive blood glucose measurement apparatus 101 and the invasive blood glucose measurement apparatus in Embodiment 1 of the present invention are plotted on the time axis at a time of 0 to 20 minutes. In FIG. 5, 401 is an approximation curve calculated on the basis of an approximation formula.

The operation when the non-invasive blood glucose measurement apparatus 101 measures blood glucose levels continuously will now be described through reference to FIGS. 1, 2, 3, and 4.

In Embodiment 1 of the present invention, measurement with the invasive blood glucose measurement apparatus is performed at 10-minute intervals, and measurement with the non-invasive blood glucose measurement apparatus 101 is repeated at six-minute intervals, with the basic measurement cycle comprising the time from when the controller 208 outputs the actuation signal 83 to the amplifier 203 and the A/D converter 204 until the blood glucose level estimator 207 calculates the estimated blood glucose level 72 and outputs it to the outside.

However, in order to minimize error in the estimated blood glucose level 72 caused by body movement (such as breathing and pulse) and external noise, a method may also be employed in which the above-mentioned basic measurement cycle is repeated a specific number of times at frequencies of about 10 µs to 100 ms, and the estimated blood glucose level 72 is calculated using this as the basic measurement cycle (this is described in detail in Embodiment 2).

The initial values of the register that can be written to from the outside are set as follows.
- 20 µJ as the minimum luminous energy level of the luminous energy level modifier 281 (minimum luminous energy level register 282)
- 20 µJ as the increase in the luminous energy level 81 of the luminous energy level modifier 281 (increased luminous energy level register 283)
- 100 µJ as the maximum luminous energy level of the luminous energy level modifier 281 (maximum luminous energy level register 284)
- 10 mg/dL as the threshold for average error between the estimated blood glucose level 72 and the blood glucose level measured with the invasive blood glucose measurement apparatus of the luminous energy level selector 271 (estimated error register A 272)
- 30 minutes as the output cycle of the switch-on timing 82 of the periodic luminous energy level checker 285 (checking cycle register A 286)
- 100 µJ as the luminous energy level 81 of the periodic luminous energy level checker 285 (checked luminous energy level register 287)
- 3 mg/dL as the error between the estimated blood glucose level measured at the luminous energy level changed by the periodic luminous energy level checker 285 of the favorable luminous energy level checker 273, and the estimated blood glucose level measured at the luminous energy level set prior to being changed with the periodic luminous energy level checker 285 (favorable error register A 274)
- 70 mg/dL as the amount of change in the blood glucose level of the invasive blood glucose measurement apparatus needed to calculate calibration data (calibration-use blood glucose threshold register 275)

First, at a time of 0 minutes, the measurement of blood glucose level that accompanies blood sampling is begun when a blood sampling switch (not shown) provided to the invasive blood glucose measurement apparatus is pressed by the user. The user takes a blood sample from the body with a puncture needle or other such blood sampling component, and the blood glucose level is measured.

Let us say that the blood glucose level at this point is 70 mg/dL.

The user inputs blood glucose measurement information 91 (such as the blood glucose level measured with an invasive blood glucose measurement apparatus) with a blood glucose measurement information input component (not shown) provided to the non-invasive blood glucose measurement apparatus 101, in order to transmit the blood glucose measurement information 91 (70 mg/dL at a time of 0 minutes) to the non-invasive blood glucose measurement apparatus 101.

The blood glucose measurement information 91 is stored in the memory 205.

Here, the blood glucose measurement information 91 measured with the invasive blood glucose measurement apparatus was inputted by the user to the non-invasive blood glucose measurement apparatus 101, but may instead be automatically transferred from the invasive blood glucose measurement apparatus to the non-invasive blood glucose measurement apparatus 101.

As shown in FIG. 1, the non-invasive blood glucose measurement apparatus 101 is placed on the body surface 102, such as an arm, after which the user actuates a blood glucose level measurement start switch (not shown) provided to the non-invasive blood glucose measurement apparatus 101. Next, the controller 208 outputs the actuation signal 83 to the amplifier 203 and the A/D converter 204, controls the switch-on timing 82 and the luminous energy level 81 of the light source 201 at a timing at which the amplifier 203 and the A/D converter 204 can operate stably, and switches on the light source 201.

At this point a value of 20 µJ is set in the minimum luminous energy level register 282 provided with the luminous energy level modifier 281. Therefore, a luminous energy level 81 of 20 µJ is outputted to the light source 201.

What is being described here is that measurement is begun in the invasive blood glucose measurement apparatus and the non-invasive blood glucose measurement apparatus 101 simultaneously when the user presses the blood sampling switch and the measurement start switch, respectively, but the measurement need not be carried out at the same time. Also, measurement may be begun by actuating first the invasive blood glucose measurement apparatus and then the non-invasive blood glucose measurement apparatus 101. Or, measurement may be begun by actuating first the non-invasive blood glucose measurement apparatus 101 and then the invasive blood glucose measurement apparatus.

The light 103 from the light source 201 propagates through the body and is absorbed by substances in the vein 104 that allow the blood glucose level to be estimated, and the photoacoustic wave signal 105 is produced.

The body information sensor 202 converts the photoacoustic wave signal 105 into a voltage signal 21. The amplifier 203 receives the actuation signal 83 from the controller 208, the voltage signal 21 converted by the body information sensor 202 is amplified at a preset gain, and this product is outputted as the amplified signal 31 to the A/D converter 204.

The reason the actuation signal 83 and the end signal 84 are inputted to the amplifier 203 here is to reduce the power consumption by the amplifier 203, so that the operation of a device such as an opamp which is a constituent element of the amplifier 203 will be enabled only at the timing at which the photoacoustic wave signal 105 is generated. Therefore, the same operation will be possible even if these signals are not inputted.

The A/D converter 204 receives the actuation signal 83 from the controller 208, the amplified signal 31 outputted from the amplifier 203 is converted back and forth into analog and digital signals at specific intervals, and the sampling data 41 is written to the memory 205.

The reason the actuation signal 83 and the end signal 84 are inputted to the A/D converter 204 here is to reduce the power consumption by the A/D converter 204, so that the operation of a device such as an AD converter which is a constituent element of the A/D converter 204 will be enabled only at the timing at which the photoacoustic wave signal 105 is generated. Therefore, the same operation will be possible even if these signals are not inputted.

The characteristic quantity detector 206 receives the end signal 84 from the controller 208, reads and analyzes the stored data 51 that has been stored in the memory 205, and calculates and stores the characteristic quantity 61 of body information.

The characteristic quantity 61 here is calculated by writing the sampling data 41 of the A/D converter 204 once to the memory 205, and reading and analyzing it with the characteristic quantity detector 206. It is clear, however, that the characteristic quantity 61 can also be calculated if the characteristic quantity detector 206 receives the sampling data 41 from the A/D) converter 204.

When the light source 201 switches on at the luminous energy level 81 of 20 μJ, and the series of operations for storing the characteristic quantity 61 is complete, the luminous energy level modifier 281 adds the luminous energy level (20 μJ) set in the increased luminous energy level register 283 to the current luminous energy level 81 (20 μJ), and compares whether the summed luminous energy level 81 (40 μJ) is greater than the maximum luminous energy level (100 μJ) set in the maximum luminous energy level register 284.

Since the summed luminous energy level 81 here does not exceed the maximum luminous energy level register 284, the controller 208 controls the luminous energy level 81 (40 μJ) and the switch-on timing 82 to switch on the light source 201.

Next, just as when the luminous energy level 81 was 20 μJ, when the light source 201 switches on at the luminous energy level 81 of 40 μJ, and the series of operations for storing the characteristic quantity 61 is complete, the luminous energy level modifier 281 adds the luminous energy level (20 μJ) set in the increased luminous energy level register 283 to the current luminous energy level 81 (40 μJ), and compares whether the summed luminous energy level 81 (60 μJ) is greater than the maximum luminous energy level (100 μJ) set in the maximum luminous energy level register 284.

Since the summed luminous energy level 81 here does not exceed the maximum luminous energy level register 284, the controller 208 controls the luminous energy level 81 (60 μJ) and the switch-on timing 82 to switch on the light source 201.

Next, just as when the luminous energy level 81 was 20 μJ, when the light source 201 switches on at the luminous energy level 81 of 60 μJ, and the series of operations for storing the characteristic quantity 61 is complete, the luminous energy level modifier 281 adds the luminous energy level (20 μJ) set in the increased luminous energy level register 283 to the current luminous energy level 81 (60 μJ), and compares whether the summed luminous energy level 81 (80 μJ) is greater than the maximum luminous energy level (100 μJ) set in the maximum luminous energy level register 284.

Since the summed luminous energy level 81 here does not exceed the maximum luminous energy level register 284, the controller 208 controls the luminous energy level 81 (80 μJ) and the switch-on timing 82 to switch on the light source 201.

Next, just as when the luminous energy level 81 was 20 μJ, when the light source 201 switches on at the luminous energy level 81 of 80 μJ, and the series of operations for storing the characteristic quantity 61 is complete, the luminous energy level modifier 281 adds the luminous energy level (20 μJ) set in the increased luminous energy level register 283 to the current luminous energy level 81 (80 μJ), and compares whether the summed luminous energy level 81 (100 μJ) is greater than the maximum luminous energy level (100 μJ) set in the maximum luminous energy level register 284.

Since the summed luminous energy level 81 here does not exceed the maximum luminous energy level register 284, the controller 208 controls the luminous energy level 81 (100 μJ) and the switch-on timing 82 to switch on the light source 201.

Next, just as when the luminous energy level 81 was 20 μJ, when the light source 201 switches on at the luminous energy level 81 of 100 μJ, and the series of operations for storing the characteristic quantity 61 is complete, the luminous energy level modifier 281 adds the luminous energy level (20 μJ) set in the increased luminous energy level register 283 to the current luminous energy level 81 (100 μJ), and compares whether the summed luminous energy level 81 (120 μJ) is greater than the maximum luminous energy level (100 μJ) set in the maximum luminous energy level register 284.

Since the summed luminous energy level 81 here exceeds the maximum luminous energy level register 284, the luminous energy level modifier 281 returns the luminous energy level 81 to the minimum luminous energy level (20 μJ) set in the minimum luminous energy level register 282, and awaits the next measurement timing with the non-invasive blood glucose measurement apparatus 101 (at 6 minutes).

Here, the luminous energy level 81 was changed from the minimum luminous energy level (20 μJ) to the maximum luminous energy level (100 μJ) according to the register group provided to the luminous energy level modifier 281 (the minimum luminous energy level register 282, the increased luminous energy level register 283, and the maximum luminous energy level register 284), but the luminous energy level 81 may instead be changed by providing a register group that sets a plurality of luminous energy levels.

At a time of 6 minutes, measurement with the non-invasive blood glucose measurement apparatus 101 is performed at 6-minute intervals, which is the same as at a time of 0 minutes. That is, the non-invasive blood glucose measurement apparatus 101 switches on the light source 201 so that the luminous energy level increases in 20-μJ intervals from 20 to 100 μJ, and the series of operations for storing the characteristic quantity 61 is performed.

When measurement at a luminous energy level 81 of 100 μJ is complete, the luminous energy level modifier 281 returns the luminous energy level 81 to the minimum luminous energy level (20 μJ) set in the minimum luminous energy level register 282, and awaits the next measurement timing with the non-invasive blood glucose measurement apparatus 101 (at 12 minutes).

At a time of 10 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 82 mg/dL. The user inputs to the non-invasive blood glucose measurement apparatus 101 the blood glucose measurement information 91 measured with the invasive blood glucose measurement apparatus (at a time of 10 minutes: 82 mg/dL).

The inputted blood glucose measurement information 91 is stored in the memory 205, inputted to the blood glucose level estimator 207, and compared with the blood glucose level at a time of 0 minutes (70 mg/dL), and a change of 12 mg/dL is calculated. Since the calculated change is less than the threshold of 70 mg/dL set in the calibration-use blood glucose threshold register 275, measurement with the invasive blood glucose measurement apparatus is continued.

At a time of 12 minutes, just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 18 minutes).

At a time of 18 minutes, just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 24 minutes).

At a time of 20 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 100 mg/dL. The user inputs to the non-invasive blood glucose measurement apparatus 101 the blood glucose measurement information 91 measured with the invasive blood glucose measurement apparatus (at a time of 20 minutes: 100 mg/dL).

The inputted blood glucose measurement information 91 is stored in the memory 205, inputted to the blood glucose level estimator 207, and compared with the blood glucose level at a time of 0 minutes (70 mg/dL), and a change of 30 mg/dL is calculated. Since the calculated change is less than the threshold of 70 mg/dL set in the calibration-use blood glucose threshold register 275, measurement with the invasive blood glucose measurement apparatus is continued.

At a time of 24 minutes, just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 30 minutes).

At a time of 30 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 118 mg/dL. The user inputs to the non-invasive blood glucose measurement apparatus 101 the blood glucose measurement information 91 measured with the invasive blood glucose measurement apparatus (at a time of 30 minutes: 118 mg/dL).

The inputted blood glucose measurement information 91 is stored in the memory 205, inputted to the blood glucose level estimator 207, and compared with the blood glucose level at a time of 0 minutes (70 mg/dL), and a change of 48 mg/dL is calculated. Since the calculated change is less than the threshold of 70 mg/dL set in the calibration-use blood glucose threshold register 275, measurement with the invasive blood glucose measurement apparatus is continued.

Just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 36 minutes).

At a time of 36 minutes, just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 42 minutes).

At a time of 40 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 125 mg/dL. The user inputs to the non-invasive blood glucose measurement apparatus 101 the blood glucose measurement information 91 measured with the invasive blood glucose measurement apparatus (at a time of 40 minutes: 125 mg/dL).

The inputted blood glucose measurement information 91 is stored in the memory 205, inputted to the blood glucose level estimator 207, and compared with the blood glucose level at a time of 0 minutes (70 mg/dL), and a change of 60 mg/dL is calculated. Since the calculated change is less than the threshold of 70 mg/dL set in the calibration-use blood glucose threshold register 275, measurement with the invasive blood glucose measurement apparatus is continued.

At a time of 42 minutes, just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 48 minutes).

At a time of 48 minutes, just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 54 minutes).

At a time of 50 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 138 mg/dL. The user inputs to the non-invasive blood glucose measurement apparatus 101 the blood glucose measurement information 91 measured with the invasive blood glucose measurement apparatus (at a time of 50 minutes: 138 mg/dL).

The inputted blood glucose measurement information 91 is stored in the memory 205, inputted to the blood glucose level estimator 207, and compared with the blood glucose level at a time of 0 minutes (70 mg/dL), and a change of 68 mg/dL is calculated. Since the calculated change is less than the threshold of 70 mg/dL set in the calibration-use blood glucose threshold register 275, measurement with the invasive blood glucose measurement apparatus is continued.

At a time of 54 minutes, just as at a time of 6 minutes, the non-invasive blood glucose measurement apparatus 101 switches on the light source 201 so that the luminous energy level increases in 20-µJ intervals from 20 to 100 µJ, and the series of operations for storing the characteristic quantity 61 is performed.

When measurement at a luminous energy level 81 of 100 µJ is complete, the luminous energy level modifier 281 returns the luminous energy level 81 to the minimum luminous energy level (20 µJ) set in the minimum luminous energy level register 282, and awaits the next measurement timing with the non-invasive blood glucose measurement apparatus 101 (at 60 minutes).

At a time of 60 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 142 mg/dL. The user inputs to the non-invasive blood glucose measurement apparatus 101 the blood glucose measurement information 91 measured with the invasive blood glucose measurement apparatus (at a time of 60 minutes: 142 mg/dL).

The inputted blood glucose measurement information 91 is stored in the memory 205, inputted to the blood glucose level estimator 207, and compared with the blood glucose level at a time of 0 minutes (70 mg/dL), and a change of 72 mg/dL is calculated. Since the calculated change is greater than the threshold of 70 mg/dL set in the calibration-use blood glucose threshold register 275, an approximation formula is calculated on the basis of the seven pieces of data for the invasive blood glucose measurement apparatus measured up to this point (70 mg/dL at a time of 0 minutes, 82 mg/dL at a time of 10 minutes, 100 mg/dL at a time of 20 minutes, 118 mg/dL at a time of 30 minutes, 125 mg/dL at a time of 40 minutes, 138 mg/dL at a time of 50 minutes, and 142 mg/dL at a time of 60 minutes), and the approximation curve 401 (see FIG. 5) is found from the approximation formula thus calculated. Also, the approximated blood glucose levels at the timings measured with the non-invasive blood glucose measurement apparatus 101 are calculated from the approximation curve 401, and calibration data is calculated for each luminous energy level on the basis of the characteristic quantity 61 of the non-invasive blood glucose measurement apparatus 101 with respect to each luminous energy level, and these approximated blood glucose levels.

The estimated blood glucose level 72 for each luminous energy level is found from a time of 0 minutes until a time of 60 minutes on the basis of the calibration data thus calculated.

When the estimated blood glucose level 72 at each measurement time is calculated on the basis of the calibration data, we obtain the following.

At a time of 0 minutes:
the estimated blood glucose level 72 at a luminous energy level of 20 µJ is 68 mg/dL,
the estimated blood glucose level 72 at a luminous energy level of 40 µJ is 69 mg/dL,
the estimated blood glucose level 72 at a luminous energy level of 60 µJ is 70 mg/dL,
the estimated blood glucose level 72 at a luminous energy level of 80 µJ is 70 mg/dL, and
the estimated blood glucose level 72 at a luminous energy level of 100 µJ is 70 mg/dL.

At a time of 6 minutes:
the estimated blood glucose level 72 at a luminous energy level of 20 µJ is 75 mg/dL,
the estimated blood glucose level 72 at a luminous energy level of 40 µJ is 76 mg/dL,
the estimated blood glucose level 72 at a luminous energy level of 60 µJ is 78 mg/dL,
the estimated blood glucose level 72 at a luminous energy level of 80 µJ is 78 mg/dL, and
the estimated blood glucose level 72 at a luminous energy level of 100 µJ is 78 mg/dL.

At a time of 12 minutes:
the estimated blood glucose level 72 at a luminous energy level of 20 µJ is 79 mg/dL,
the estimated blood glucose level 72 at a luminous energy level of 40 µJ is 80 mg/dL,
the estimated blood glucose level 72 at a luminous energy level of 60 µJ is 83 mg/dL, the estimated blood glucose level 72 at a luminous energy level of 80 µJ is 85 mg/dL, and the estimated blood glucose level 72 at a luminous energy level of 100 µJ is 87 mg/dL.

At a time of 18 minutes:

the estimated blood glucose level 72 at a luminous energy level of 20 µJ is 80 mg/dL, the estimated blood glucose level 72 at a luminous energy level of 40 µJ is 82 mg/dL, the estimated blood glucose level 72 at a luminous energy level of 60 µJ is 85 mg/dL, the estimated blood glucose level 72 at a luminous energy level of 80 µJ is 88 mg/dL, and the estimated blood glucose level 72 at a luminous energy level of 100 µJ is 92 mg/dL.

At a time of 24 minutes:

the estimated blood glucose level 72 at a luminous energy level of 20 µJ is 82 mg/dL, the estimated blood glucose level 72 at a luminous energy level of 40 µJ is 83 mg/dL, the estimated blood glucose level 72 at a luminous energy level of 60 µJ is 92 mg/dL, the estimated blood glucose level 72 at a luminous energy level of 80 µJ is 105 mg/dL, and the estimated blood glucose level 72 at a luminous energy level of 100 µJ is 108 mg/dL.

At a time of 30 minutes:

the estimated blood glucose level 72 at a luminous energy level of 20 µJ is 83 mg/dL, the estimated blood glucose level 72 at a luminous energy level of 40 µJ is 85 mg/dL, the estimated blood glucose level 72 at a luminous energy level of 60 µJ is 98 mg/dL, the estimated blood glucose level 72 at a luminous energy level of 80 µJ is 113 mg/dL, and the estimated blood glucose level 72 at a luminous energy level of 100 µJ is 115 mg/dL.

At a time of 36 minutes:

the estimated blood glucose level 72 at a luminous energy level of 20 µJ is 83 mg/dL, the estimated blood glucose level 72 at a luminous energy level of 40 µJ is 88 mg/dL, the estimated blood glucose level 72 at a luminous energy level of 60 µJ is 105 mg/dL, the estimated blood glucose level 72 at a luminous energy level of 80 µJ is 117 mg/dL, and the estimated blood glucose level 72 at a luminous energy level of 100 µJ is 119 mg/dL.

At a time of 42 minutes:

the estimated blood glucose level 72 at a luminous energy level of 20 µJ is 82 mg/dL, the estimated blood glucose level 72 at a luminous energy level of 40 µJ is 90 mg/dL, the estimated blood glucose level 72 at a luminous energy level of 60 µJ is 110 mg/dL, the estimated blood glucose level 72 at a luminous energy level of 80 µJ is 128 mg/dL, and the estimated blood glucose level 72 at a luminous energy level of 100 µJ is 129 mg/dL.

At a time of 48 minutes:

the estimated blood glucose level 72 at a luminous energy level of 20 µJ is 84 mg/dL, the estimated blood glucose level 72 at a luminous energy level of 40 µJ is 92 mg/dL, the estimated blood glucose level 72 at a luminous energy level of 60 µJ is 115 mg/dL, the estimated blood glucose level 72 at a luminous energy level of 80 µJ is 133 mg/dL, and the estimated blood glucose level 72 at a luminous energy level of 100 µJ is 134 mg/dL.

At a time of 54 minutes:

the estimated blood glucose level 72 at a luminous energy level of 20 µJ is 85 mg/dL, the estimated blood glucose level 72 at a luminous energy level of 40 µJ is 95 mg/dL, the estimated blood glucose level 72 at a luminous energy level of 60 µJ is 123 mg/dL, the estimated blood glucose level 72 at a luminous energy level of 80 µJ is 138 mg/dL, and the estimated blood glucose level 72 at a luminous energy level of 100 µJ is 138 mg/dL.

At a time of 60 minutes:

the estimated blood glucose level 72 at a luminous energy level of 20 µJ is 85 mg/dL, the estimated blood glucose level 72 at a luminous energy level of 40 µJ is 100 mg/dL, the estimated blood glucose level 72 at a luminous energy level of 60 µJ is 133 mg/dL, the estimated blood glucose level 72 at a luminous energy level of 80 µJ is 142 mg/dL, and the estimated blood glucose level 72 at a luminous energy level of 100 µJ is 142 mg/dL.

Next, the luminous energy level selector 271 calculates the error by comparing the estimated blood glucose levels 72 from the non-invasive blood glucose measurement apparatus for each luminous energy level from a time of 0 minutes until a time of 60 minutes, with the blood glucose levels from the invasive blood glucose measurement apparatus or, when no blood glucose levels have been measured, the approximated blood glucose levels.

When the error is calculated at each measurement time, we obtain the following.

At a time of 0 minutes, the blood glucose level from the invasive blood glucose measurement apparatus is 70 mg/dL, so the error from the estimated blood glucose level 72 at a luminous energy level of 20 µJ is 2 mg/dL, the error from the estimated blood glucose level 72 at a luminous energy level of 40 µJ is 1 mg/dL, the error from the estimated blood glucose level 72 at a luminous energy level of 60 µJ is 0 mg/dL, the error from the estimated blood glucose level 72 at a luminous energy level of 80 µJ is 0 mg/dL, and the error from the estimated blood glucose level 72 at a luminous energy level of 100 µJ is 0 mg/dL.

At a time of 6 minutes, the approximated blood glucose level from the invasive blood glucose measurement apparatus is 78 mg/dL, so the error from the estimated blood glucose level 72 at a luminous energy level of 20 µJ is 3 mg/dL, the error from the estimated blood glucose level 72 at a luminous energy level of 40 µJ is 2 mg/dL, the error from the estimated blood glucose level 72 at a luminous energy level of 60 µJ is 0 mg/dL, the error from the estimated blood glucose level 72 at a luminous energy level of 80 µJ is 0 mg/dL, and the error from the estimated blood glucose level 72 at a luminous energy level of 100 µJ is 0 mg/dL.

At a time of 12 minutes, the approximated blood glucose level from the invasive blood glucose measurement apparatus is 89 mg/dL, so the error from the estimated blood glucose level 72 at a luminous energy level of 20 µJ is 10 mg/dL, the error from the estimated blood glucose level 72 at a luminous energy level of 40 μJ is 9 mg/dL, the error from the estimated blood glucose level 72 at a luminous energy level of 60 μJ is 6 mg/dL, the error from the estimated blood glucose level 72 at a luminous energy level of 80 μJ is 4 mg/dL, and the error from the estimated blood glucose level 72 at a luminous energy level of 100 μJ is 2 mg/dL.

At a time of 18 minutes, the approximated blood glucose level from the invasive blood glucose measurement apparatus is 98 mg/dL, so the error from the estimated blood glucose level 72 at a luminous energy level of 20 μJ is 18 mg/dL, the error from the estimated blood glucose level 72 at a luminous energy level of 40 μJ is 16 mg/dL, the error from the estimated blood glucose level 72 at a luminous energy level of 60 μJ is 13 mg/dL, the error from the estimated blood glucose level 72 at a luminous energy level of 80 μJ is 10 mg/dL, and the error from the estimated blood glucose level 72 at a luminous energy level of 100 μJ is 6 mg/dL.

At a time of 24 minutes, the approximated blood glucose level from the invasive blood glucose measurement apparatus is 107 mg/dL, so the error from the estimated blood glucose level 72 at a luminous energy level of 20 μJ is 25 mg/dL, the error from the estimated blood glucose level 72 at a luminous energy level of 40 μJ is 24 mg/dL, the error from the estimated blood glucose level 72 at a luminous energy level of 60 μJ is 15 mg/dL, the error from the estimated blood glucose level 72 at a luminous energy level of 80 μJ is 2 mg/dL, and the error from the estimated blood glucose level 72 at a luminous energy level of 100 μJ is 1 mg/dL.

At a time of 30 minutes, the approximated blood glucose level from the invasive blood glucose measurement apparatus is 118 mg/dL, so the error from the estimated blood glucose level 72 at a luminous energy level of 20 μJ is 35 mg/dL, the error from the estimated blood glucose level 72 at a luminous energy level of 40 μJ is 33 mg/dL, the error from the estimated blood glucose level 72 at a luminous energy level of 60 μJ is 20 mg/dL, the error from the estimated blood glucose level 72 at a luminous energy level of 80 μJ is 5 mg/dL, and the error from the estimated blood glucose level 72 at a luminous energy level of 100 μJ is 3 mg/dL.

At a time of 36 minutes, the approximated blood glucose level from the invasive blood glucose measurement apparatus is 122 mg/dL, so the error from the estimated blood glucose level 72 at a luminous energy level of 20 μJ is 39 mg/dL, the error from the estimated blood glucose level 72 at a luminous energy level of 40 μJ is 37 mg/dL, the error from the estimated blood glucose level 72 at a luminous energy level of 60 μJ is 24 mg/dL, the error from the estimated blood glucose level 72 at a luminous energy level of 80 μJ is 9 mg/dL, and the error from the estimated blood glucose level 72 at a luminous energy level of 100 μJ is 7 mg/dL.

At a time of 42 minutes, the approximated blood glucose level from the invasive blood glucose measurement apparatus is 128 mg/dL, so the error from the estimated blood glucose level 72 at a luminous energy level of 20 μJ is 46 mg/dL, the error from the estimated blood glucose level 72 at a luminous energy level of 40 μJ is 38 mg/dL, the error from the estimated blood glucose level 72 at a luminous energy level of 60 μJ is 18 mg/dL, the error from the estimated blood glucose level 72 at a luminous energy level of 80 μJ is 0 mg/dL, and the error from the estimated blood glucose level 72 at a luminous energy level of 100 μJ is 1 mg/dL.

At a time of 48 minutes, the approximated blood glucose level from the invasive blood glucose measurement apparatus is 133 mg/dL, so the error from the estimated blood glucose level 72 at a luminous energy level of 20 μJ is 49 mg/dL, the error from the estimated blood glucose level 72 at a luminous energy level of 40 μJ is 41 mg/dL, the error from the estimated blood glucose level 72 at a luminous energy level of 60 μJ is 18 mg/dL, the error from the estimated blood glucose level 72 at a luminous energy level of 80 μJ is 0 mg/dL, and the error from the estimated blood glucose level 72 at a luminous energy level of 100 μJ is 1 mg/dL.

At a time of 54 minutes, the approximated blood glucose level from the invasive blood glucose measurement apparatus is 138 mg/dL, so the error from the estimated blood glucose level 72 at a luminous energy level of 20 μJ is 53 mg/dL, the error from the estimated blood glucose level 72 at a luminous energy level of 40 μJ is 43 mg/dL, the error from the estimated blood glucose level 72 at a luminous energy level of 60 μJ is 15 mg/dL, the error from the estimated blood glucose level 72 at a luminous energy level of 80 μJ is 0 mg/dL, and the error from the estimated blood glucose level 72 at a luminous energy level of 100 μJ is 0 mg/dL.

At a time of 60 minutes, the approximated blood glucose level from the invasive blood glucose measurement apparatus is 142 mg/dL, so the error from the estimated blood glucose level 72 at a luminous energy level of 20 μJ is 57 mg/dL, the error from the estimated blood glucose level 72 at a luminous energy level of 40 μJ is 42 mg/dL, the error from the estimated blood glucose level 72 at a luminous energy level of 60 μJ is 90 mg/dL, the error from the estimated blood glucose level 72 at a luminous energy level of 80 μJ is 0 mg/dL, and the error from the estimated blood glucose level 72 at a luminous energy level of 100 μJ is 0 mg/dL.

Next, the luminous energy level selector 271 calculates the average error for each luminous energy level, and outputs the smallest luminous energy level at which the calculated average error is under the preset estimated error register A 272, as the luminous energy level command signal 71.

The average error for each luminous energy level is:

31 mg/dL at a luminous energy level of 20 μJ,
26 mg/dL at a luminous energy level of 40 μJ,
12 mg/dL at a luminous energy level of 60 μJ,
2.4 mg/dL at a luminous energy level of 80 μJ, and
1.5 mg/dL at a luminous energy level of 100 μJ.

The luminous energy level selector 271 outputs the smallest luminous energy level of 80 μJ, at which the calculated average error is under the average threshold for error preset in the estimated error register A 272 (10 mg/dL), as the luminous energy level command signal 71, and outputs the estimated blood glucose level 72 to the outside.

When the luminous energy level command signal 71 outputted from the blood glucose level estimator 207 is inputted to the controller 208, the luminous energy level modifier 281 changes the luminous energy level 81 used for the normal measurement period to 80 μJ according to the luminous energy level command signal 71.

The periodic luminous energy level checker 285 begins measurement of elapsed time when the luminous energy level command signal 71 is detected.

In the description here, the calculated calibration data is used to calculate the estimated blood glucose level 72 from a time of 0 minutes up to a time of 60 minutes, the average error between the blood glucose levels from the invasive blood glucose measurement apparatus and the estimated blood glucose levels 72 at the various measurement times is found, and the luminous energy level 81 used in the normal measurement period is determined, but another method may be used instead, such as determining the luminous energy level 81 used in the normal measurement period by finding the error at the timing at which the calibration data is calculated, or determining the luminous energy level 81 used in the normal measurement period by using the results during the calibration period.

When the calibration period is complete, the normal measurement period begins, and from a time of 66 minutes onward, measurement is performed with the non-invasive blood glucose measurement apparatus every six minutes (cycle).

At a time of 66 minutes, the elapsed time is 6 minutes.

Here, the elapsed time does not exceed the 30 minutes preset in the checking cycle register A 286, so the controller 208 controls the switch-on timing 82 and the luminous energy level 81 (80 μJ) determined in the calibration period, the light source 201 is switched on, the characteristic quantity 61 of body information is calculated from the photoacoustic wave signal 105 generated by the light 103 from substances in the vein 104 that allow the blood glucose level to be estimated, and the estimated blood glucose level 72 based on the calibration data is found from the characteristic quantity 61 calculated by the blood glucose level estimator 207. The series of processing involving output to the outside is the same as in the calibration period.

From a time of 72 minutes onward, measurement is performed every six minutes with the non-invasive blood glucose measurement apparatus in the same manner as at an elapsed time of 66 minutes until the elapsed time exceeds 30 minutes.

At a time of 96 minutes, the elapsed time is 36 times.

Since the elapsed time here exceeds the 30 minutes preset in the checking cycle register A 286, the controller 208 calculates the estimated blood glucose level 72 at the luminous energy level 81 determined in the calibration period (80 μJ), after which the periodic luminous energy level checker 285 performs measurement of the estimated blood glucose level 72 at the luminous energy level 81 preset in the checked luminous energy level register 287 (100 μJ).

First, the controller 208 controls the luminous energy level 81 (80 μJ) and the switch-on timing 82 to switch on the light source 201, calculates the characteristic quantity 61 of body information from the photoacoustic wave signal 105 generated by the light 103 from substances in the vein 104 that allow the blood glucose level to be estimated, and finds the estimated blood glucose level 72 based on the calibration data from the characteristic quantity 61 calculated by the blood glucose level estimator 207. Let us say that the estimated blood glucose level 72 at 80 μJ here is 162 mg/dL.

Next, the periodic luminous energy level checker 285 switches on the light source 201 at the luminous energy level 81 of 100 μJ preset in the checked luminous energy level register 287, the elapsed time that has been counted up to this point is reset, and measurement of the elapsed time is started over. The characteristic quantity 61 of body information is calculated from the photoacoustic wave signal 105 generated by the light 103 from the light source 201 from substances in the vein 104 that allow the blood glucose level to be estimated, and the estimated blood glucose level 72 based on the calibration data for 100 μJ calculated during the calibration period is found from the characteristic quantity 61 calculated by the blood glucose level estimator 207. Let us say that the estimated blood glucose level 72 at 100 μJ here is 163 mg/dL.

The favorable luminous energy level checker 273 provided to the blood glucose level estimator 207 calculates the error (1 mg/dL) by comparing the estimated blood glucose level (162 mg/dL) at a luminous energy level of 80 μJ with the estimated blood glucose level (163 mg/dL) at a luminous energy level of 100 μJ, and determines whether or not this error is at or under the 3 mg/dL preset in the favorable error register A 274. Since the error is under the preset favorable error register A 274, the luminous energy level restoration signal 73 is outputted to the controller 208 so as to return to the luminous energy level (80 μJ) set before being changed by the periodic luminous energy level checker 285. If the determination made by the favorable luminous energy level checker 273 is that the error is greater than the favorable error register A 274 that was preset, the luminous energy level restoration signal 73 is not outputted.

When the controller 208 detects the luminous energy level restoration signal 73 outputted from the blood glucose level estimator 207, the luminous energy level modifier 281 returns the luminous energy level 81 to 80 μJ according to the luminous energy level restoration signal 73. If no luminous energy level restoration signal 73 can be detected, subsequent measurement is performed at the luminous energy level 81 changed by the periodic luminous energy level checker 285 (the 100 μJ preset in the checked luminous energy level register 287).

Every six minutes from a time of 102 minutes onward, just as at a time of 66 minutes, measurement of the estimated blood glucose level 72 is performed at a luminous energy level of 80 μJ until the elapsed time exceeds the 30 minutes preset in the checking cycle register A 286.

Thus, with the non-invasive body information measurement apparatus pertaining to Embodiment 1 of the present invention, measurement with the non-invasive blood glucose measurement apparatus 101 in the calibration period is performed at a plurality of luminous energy levels, a plurality of estimated blood glucose levels are calculated from the plurality of characteristic quantities calculated at the various luminous energy levels and from the blood glucose levels measured with an invasive blood glucose measurement apparatus, upon completion of the calibration period the plurality of estimated blood glucose levels are compared with the blood glucose levels measured with the invasive blood glucose measurement apparatus, and measurement is performed in the normal measurement period at the smallest luminous energy level at which the calculated average error is under a preset threshold, so power consumption can be reduced compared to when measuring at a higher-output luminous energy level, regardless of the user's body condition, and the continuous measurement time can be greatly extended when the apparatus is used as a portable device.

Also, in Embodiment 1 of the present invention, it was explained that measurement in the normal measurement period was performed at the smallest luminous energy level at which the average error calculated by comparing a plurality of estimated blood glucose levels with the blood glucose levels measured with an invasive blood glucose measurement apparatus and calculated upon completion of the calibration period, that was under a preset threshold, but instead an approximation curve may be found for the average error for each luminous energy level, the luminous energy level that is under the threshold newly calculated, and the luminous energy level to be used in the normal measurement period calculated. Here again the same effect as above will be obtained.

Also, in Embodiment 1 of the present invention, the non-invasive blood glucose measurement apparatus 101 was assumed to be an apparatus that made use of photoacoustics, but may instead be another apparatus for finding blood glucose levels non-invasively. Here again the same effect as above will be obtained.

Embodiment 2

In Embodiment 2 of the present invention, the non-invasive body information measurement apparatus is assumed to be a non-invasive blood glucose measurement apparatus 101.

Figure 6:
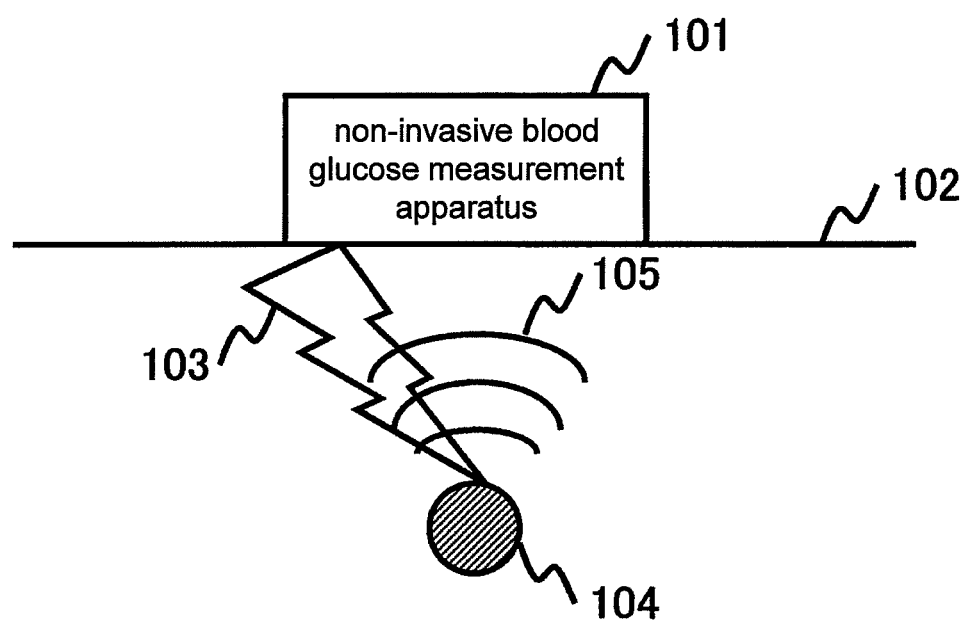
FIG. 6 illustrates the system configuration in Embodiment 2 of the present invention.
Figure 7:
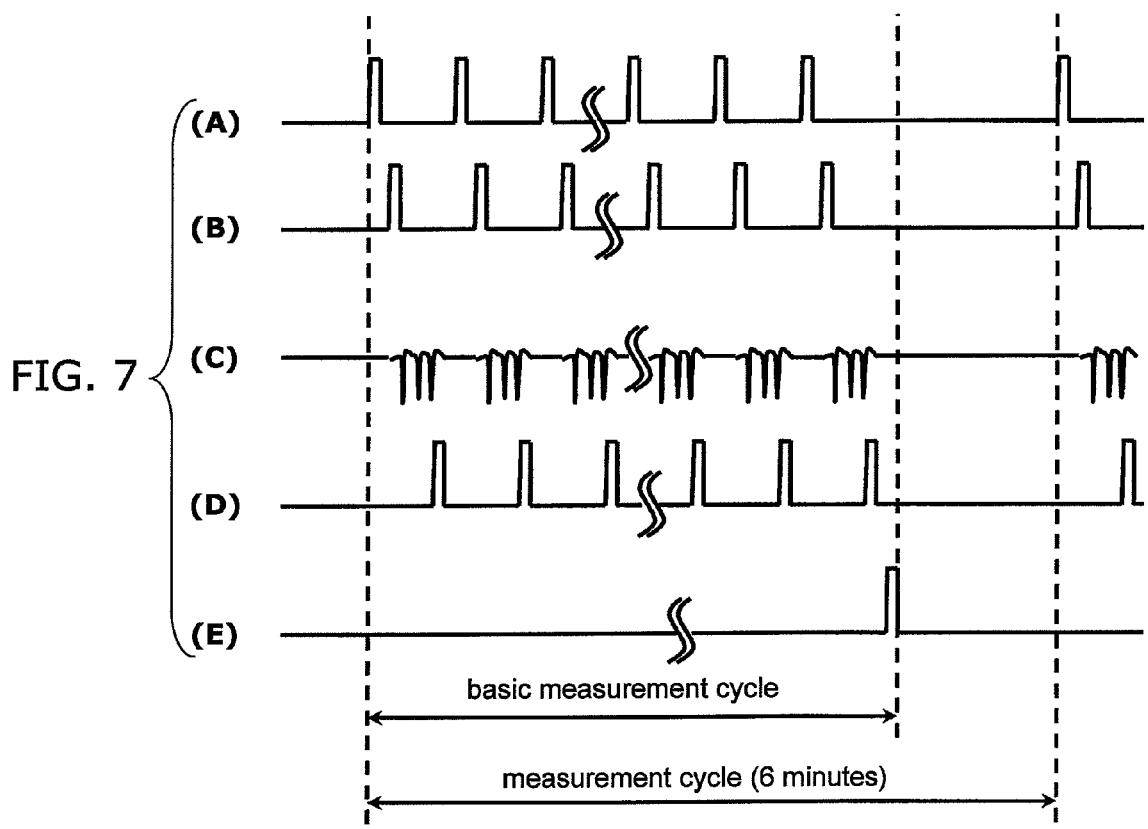
FIG. 7 illustrates the system configuration in Embodiment 2 of the present invention.

FIGS. 6 and 7 illustrate the system configuration in Embodiment 2 of the present invention. In FIG. 6, 101 is a non-invasive blood glucose measurement apparatus, 102 is a body surface, 103 is light, 104 is a vein, and 105 is an photoacoustic wave signal. In FIG. 7, (A) is an actuation signal 83, (B) is the switch-on timing 82, (C) is the photoacoustic wave signal 105, (D) is an end signal 84, and (E) is the timing at which an estimated blood glucose level is calculated. Repeated measurement is carried out, with the basic measurement cycle being the time during which a blood glucose level is estimated, and a series of operations is performed for every measurement cycle.

The non-invasive blood glucose measurement apparatus 101 is placed directly on the body surface 102, and the light 103 emitted from the non-invasive blood glucose measurement apparatus 101 is shined on the body. The light 103 propagates through the body and is absorbed by substances in the vein 104 that allow the blood glucose level to be estimated, and the photoacoustic wave signal 105 is produced.

The non-invasive blood glucose measurement apparatus 101 detects the photoacoustic wave signal 105 produced by the substances in the vein 104 that allow the blood glucose level to be estimated, and estimates the blood glucose level, which is a characteristic quantity of body information.

Figure 8:
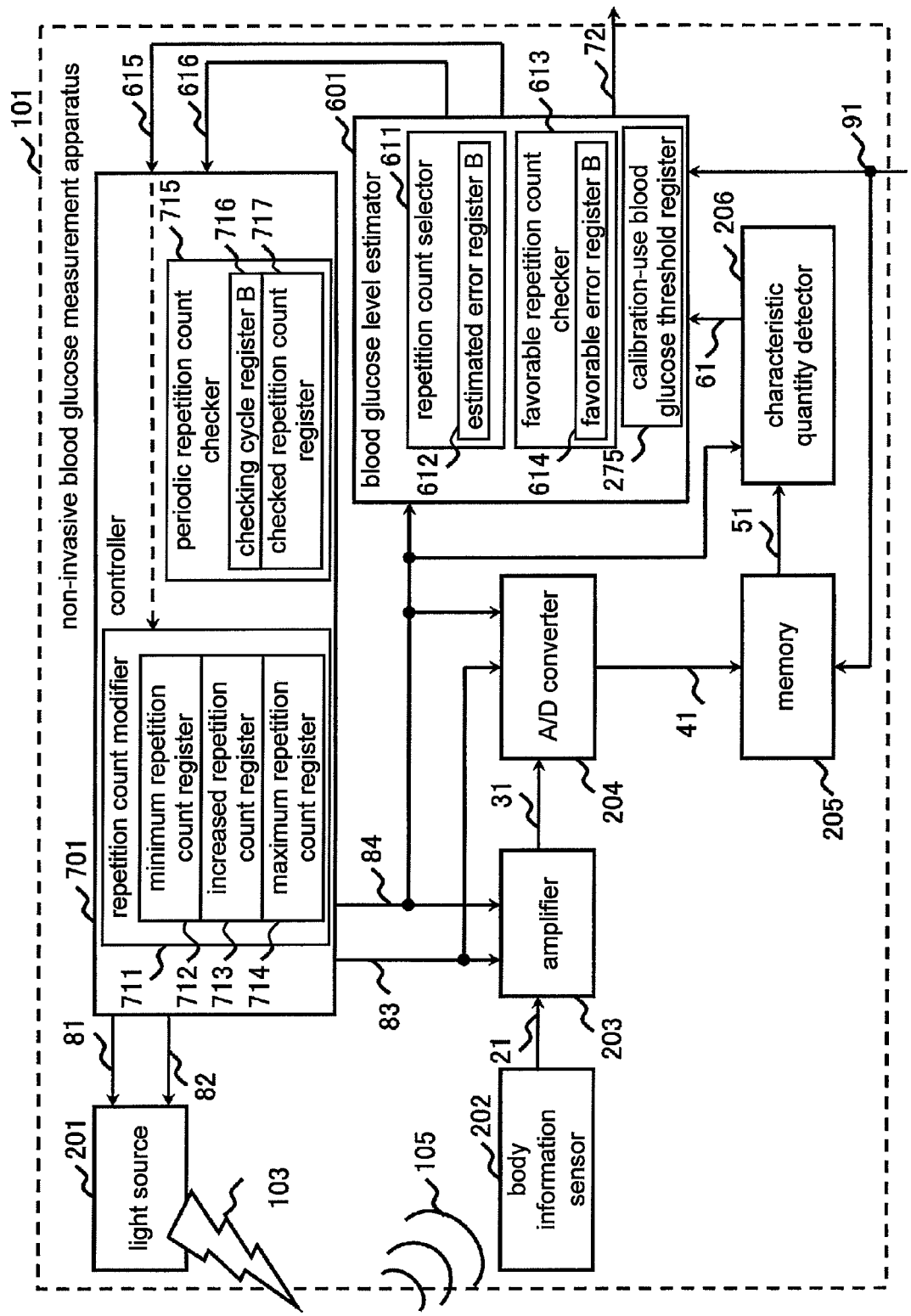
FIG. 8 is a block diagram of the non-invasive blood glucose measurement apparatus in Embodiment 2 of the present invention.

FIG. 8 is a block diagram of the configuration of the non-invasive blood glucose measurement apparatus 101 in Embodiment 2 of the present invention. In FIG. 8, the non-invasive blood glucose measurement apparatus 101 comprises a light source 201, a body information sensor 202, an amplifier 203, an A/D converter 204, a memory 205, a characteristic quantity detector 206, a blood glucose level estimator 601, and a controller 701.

The light source 201 emits the light 103, which has a wavelength that absorbs substances in the vein 104 that allow the blood glucose level to be estimated. One or more light sources 201 are provided. The controller 208 comprises a repetition count modifier 711 and a periodic repetition count checker 715, and changes the switch-on timing 82 of the light source 201 according to a repetition count command signal 615, controls the luminous energy level 81 of the light source 201, and outputs the actuation signal 83 to the amplifier 203 and the A/D converter 204, and the end signal 84 to the amplifier 203, the A/D converter 204, the characteristic quantity detector 206, and the blood glucose level estimator 207.

The repetition count modifier 711 outputs to the light source 201 the switch-on timing 82 according to the repetition count command signal 615 outputted from the blood glucose level estimator 207.

During the normal measurement period, the periodic repetition count checker 715 changes the switch-on timing 82 to a repetition count preset in a checking repetition count register 717 at a cycle preset in a checking cycle register A 286, and outputs this to the light source 201.

The body information sensor 202 converts the photoacoustic wave signal 105 into a voltage signal 21. The amplifier 203 detects the voltage signal 21 on the basis of the actuation signal 83 from the controller 208, and produces an amplified signal 31.

The A/D converter 204 converts the amplified signal 31 into sampling data 41 on the basis of the actuation signal 83 form the controller 208.

The memory 205 is written by the A/D converter 204 in the region where the sampling data 41 is to be stored, and is read by the characteristic quantity detector 206.

The series of operations until the light source 201 is switched on and the sampling data 41 is stored is repeated a specific number of times.

The characteristic quantity detector 206 averages the stored data 51 obtained in a specific number of times, analyzes the averaged data, and calculates a characteristic quantity 61 for body information.

The blood glucose level estimator 207 is made up of a repetition count selector 611 and a favorable repetition count checker 613, calculates calibration data when the amount of change in the blood glucose level measured with an invasive blood glucose measurement apparatus (not shown) has reached or exceeded a threshold preset in a calibration-use blood glucose threshold register 275, finds an estimated blood glucose level 72 from the characteristic quantity 61 calculated by the characteristic quantity detector 206 and the blood glucose level measured by the invasive blood glucose measurement apparatus, on the basis of the calculated calibration data, and outputs this to the outside.

The repetition count selector 611 calculates the average error after comparing the plurality of estimated blood glucose levels with the blood glucose levels measured with the invasive blood glucose measurement apparatus, detects the smallest repetition count at which the average error is under a threshold preset in an estimated error register B 612, and outputs the repetition count command signal 615.

The favorable repetition count checker 613 compares the estimated blood glucose levels measured at the repetition count changed by the periodic repetition count checker 715, with the estimated blood glucose levels measured at the repetition count that was set prior to being changed by the periodic repetition count checker 715, and calculates the error. The favorable repetition count checker 613 also determines whether or not the error is at or under the threshold preset in a favorable error register B 614, and if the error is at or under this threshold, a repetition count restoration signal 616 is outputted to the controller 208 so as to return to the repetition count that was set prior to being changed by the periodic repetition count checker 715.

Figure 9:
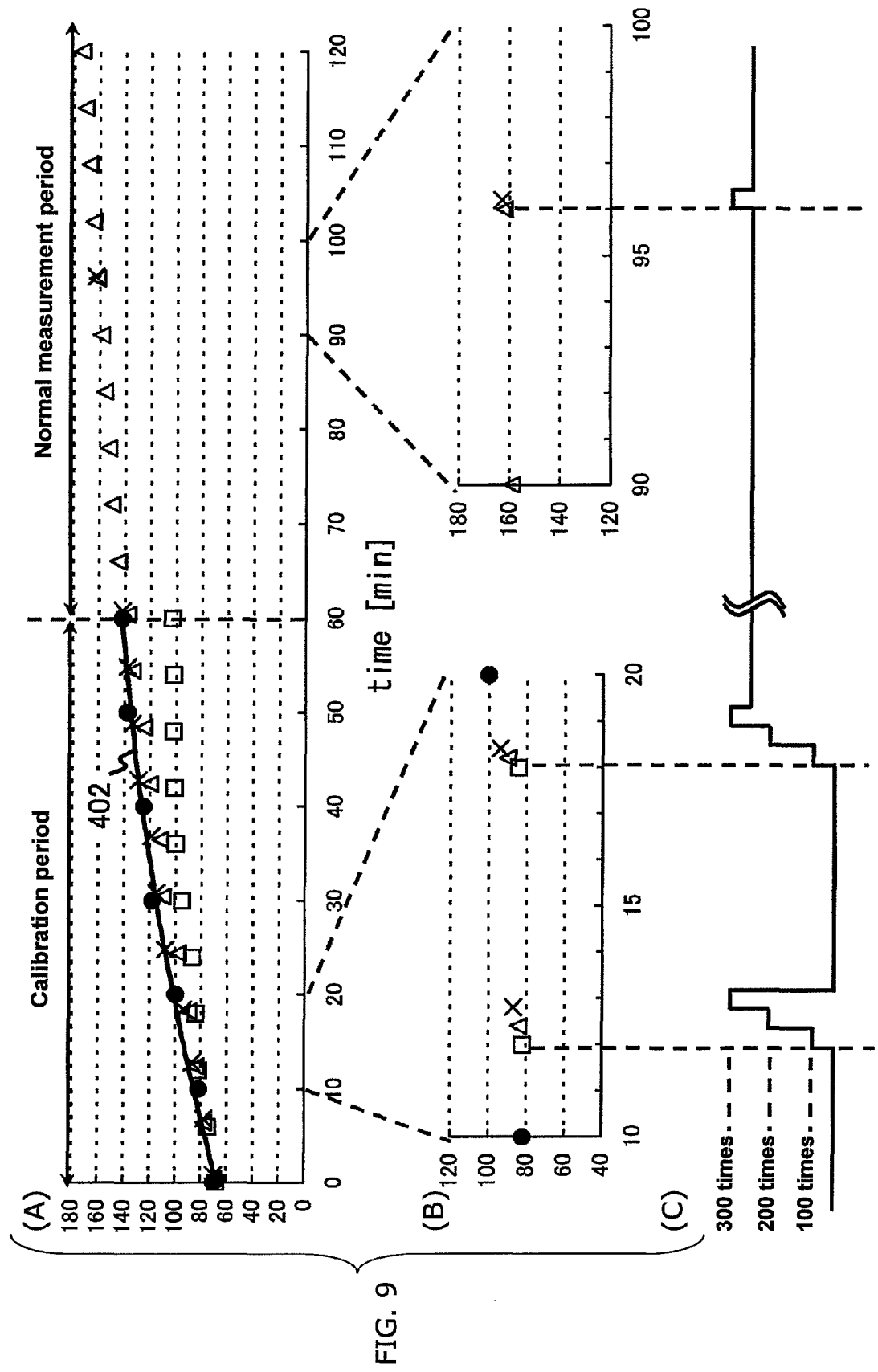
FIG. 9 is a graph in which the estimated blood glucose levels of the non-invasive blood glucose measurement apparatus in Embodiment 2 of the present invention are plotted on a time axis.

FIG. 9 shows the estimated blood glucose level 72 of the non-invasive blood glucose measurement apparatus 101 in Embodiment 2 of the present invention plotted on a time axis. In FIG. 9, (A) is the estimated blood glucose level 72, (B) is an enlarged view of the estimated blood glucose level 72 (at a time of 10 to 20 minutes, and at a time of 90 to 100 minutes), and (C) is the repetition count.

The operation when the non-invasive blood glucose measurement apparatus 101 measures blood glucose levels continuously will now be described through reference to FIGS. 6, 7, 8, and 9.

In Embodiment 2 of the present invention, measurement with the invasive blood glucose measurement apparatus is performed at 10-minute intervals, and measurement with the non-invasive blood glucose measurement apparatus 101 is repeated at six-minute intervals, with the basic measurement cycle comprising the time from when the controller 208 outputs the first actuation signal 83 to the amplifier 203 and the A/D converter 204 until the blood glucose level estimator 207 calculates the estimated blood glucose level 72 and outputs it to the outside.

The initial values of the register that can be written to from the outside are set as follows.

100 times as the minimum repetition count of the repetition count modifier 711 (minimum repetition count register 712)

100 times as the increase in the repetition count of the repetition count modifier 711 (increased repetition count register 713)

300 times as the maximum repetition count of the repetition count modifier 711 (maximum repetition count register 714)

10 mg/dL as the average threshold for the error between the estimated blood glucose level 72 and the blood glucose level measured by the invasive blood glucose measurement apparatus of the repetition count selector 611 (estimated error register B 612)

30 minutes as the cycle for changing the repetition count of the periodic repetition count checker 715 (checking cycle register B 716)

300 times as the repetition count of the periodic repetition count checker 715 (checking repetition count register B717)

3 mg/dL as the error between the estimated blood glucose level measured at the repetition count changed by the periodic repetition count checker 715 of the favorable repetition count checker 613, and the estimated blood glucose level measured at the repetition count set prior to being changed by the periodic repetition count checker 715 (favorable error register B 614)

70 mg/dL is set as the amount of change in the blood glucose level of the invasive blood glucose measurement apparatus required to calculate the calibration data (calibration-use blood glucose threshold register 275).

First, at a time of 0 minutes, the measurement of blood glucose level that accompanies blood sampling is begun when a blood sampling switch (not shown) provided to the invasive blood glucose measurement apparatus is pressed by the user. The user takes a blood sample from the body with a puncture needle or other such blood sampling component, and the blood glucose level is measured.

Let us say that the blood glucose level at this point is 70 mg/dL.

The user inputs blood glucose measurement information 91 (such as the blood glucose level measured with an invasive blood glucose measurement apparatus) with a blood glucose measurement information input component (not shown) provided to the non-invasive blood glucose measurement apparatus 101, in order to transmit the blood glucose measurement information 91 (70 mg/dL at a time of 0 minutes) to the non-invasive blood glucose measurement apparatus 101.

The inputted blood glucose measurement information 91 is stored in the memory 205.

Here, the blood glucose measurement information 91 measured with the invasive blood glucose measurement apparatus was inputted by the user to the non-invasive blood glucose measurement apparatus 101, but may instead be automatically transferred from the invasive blood glucose measurement apparatus to the non-invasive blood glucose measurement apparatus 101.

As shown in FIG. 6, the non-invasive blood glucose measurement apparatus 101 is placed on the body surface 102, such as an arm, after which the user actuates a blood glucose level measurement start switch (not shown) provided to the non-invasive blood glucose measurement apparatus 101. Next, the controller 208 outputs the actuation signal 83 to the amplifier 203 and the A/D converter 204, controls the switch-on timing 82 and the luminous energy level 81 of the light source 201 at a timing at which the amplifier 203 and the A/D converter 204 can operate stably, and switches on the light source 201.

At this point a value of 100 times is set in the minimum repetition count register 712 provided with the repetition count modifier 711, and the controller 701 counts the number of times the light source 201 is switched on until 100 times is reached.

What is being described here is that measurement is begun in the invasive blood glucose measurement apparatus and the non-invasive blood glucose measurement apparatus 101 simultaneously when the user presses the blood sampling switch and the measurement start switch, respectively, but the measurement need not be carried out at the same time. Also, measurement may be begun by actuating first the invasive blood glucose measurement apparatus and then the non-invasive blood glucose measurement apparatus 101. Or, measurement may be begun by actuating first the non-invasive blood glucose measurement apparatus 101 and then the invasive blood glucose measurement apparatus.

The light 103 from the light source 201 propagates through the body and is absorbed by substances in the vein 104 that allow the blood glucose level to be estimated, and the photoacoustic wave signal 105 is produced.

The body information sensor 202 converts the photoacoustic wave signal 105 into a voltage signal 21.

The amplifier 203 receives the actuation signal 83 from the controller 208, amplifies the voltage signal 21 converted by the body information sensor 202 at a preset gain, and this product is outputted as the amplified signal 31 to the A/D converter 204.

The reason the actuation signal 83 and the end signal 84 are inputted to the amplifier 203 here is to reduce the power consumption by the amplifier 203, so that the operation of a device such as an opamp which is a constituent element of the amplifier 203 will be enabled only at the timing at which the photoacoustic wave signal 105 is generated. Therefore, the same operation will be possible even if these signals are not inputted.

The A/D converter 204 receives the actuation signal 83 from the controller 208, the amplified signal 31 outputted from the amplifier 203 is converted back and forth into analog and digital signals at specific intervals, and the sampling data 41 is written to the memory 205.

The reason the actuation signal 83 and the end signal 84 are inputted to the A/D converter 204 here is to reduce the power consumption by the A/D converter 204, so that the operation of a device such as an AD converter which is a constituent element of the A/D converter 204 will be enabled only at the timing at which the photoacoustic wave signal 105 is generated. Therefore, the same operation will be possible even if these signals are not inputted.

The series of operations from the switching on the light source 201 until the sampling data 41 is stored is repeated 100 times, and the characteristic quantity detector 206 that has received the end signal 84 from the controller 701 reads the 100 pieces of stored data 51 in the memory 205, averages the data, and analyzes the averaged data. The characteristic quantity detector 206 then calculates the characteristic quantity 61 of body information when the repetition count is 100 times, and stores this characteristic quantity 61.

When the switching-on count reaches 100 times, the repetition count modifier 711 compares whether the number of times the light source has been switched on has reached or exceeded the repetition count set in the maximum repetition count register 714 (300 times).

When the switching-on count is less than the maximum repetition count register 714, the repetition count modifier 711 continues controlling the switch-on timing 82 of the light source 201 for the increase in the repetition count set in the increased repetition count register 713 (100 times), and switches on the light source 201 until the switching-on count reaches 200 times. The series of operations from the switching on the light source 201 until the sampling data 41 is repeated for each set of data.

The characteristic quantity detector 206 receives the end signal 84 from the controller 701, reads and averages the 200 pieces of stored data 51 that have been stored in the memory 205, and analyzes the averaged data. The characteristic quantity detector 206 then calculates the characteristic quantity 61 for body information at a repetition count of 200 times, and stores this characteristic quantity 61.

When the switching-on count reaches 200 times, the repetition count modifier 711 compares whether the switching-on count has reached or exceeded the repetition count set in the maximum repetition count register 714 (300 times).

Here, since the switching-on count is less than the maximum repetition count register 714, the repetition count modifier 711 continues controlling the switch-on timing 82 for the increase in the repetition count set in the increased repetition count register 713 (100 times), and switches on the light source 201 until the switching-on count reaches 300 times. The series of operations from the switching on the light source 201 until the sampling data 41 is repeated for each set of data.

The characteristic quantity detector 206 receives the end signal 84 from the controller 701, reads and averages the 300 pieces of stored data 51 that have been stored in the memory 205, and analyzes the averaged data. The characteristic quantity detector 206 then calculates the characteristic quantity 61 for body information at a repetition count of 300 times, and stores this characteristic quantity 61.

When the repetition count reaches 300 times, the repetition count modifier 711 compares whether the switching-on count has reached or exceeded the repetition count set in the maximum repetition count register 714 (300 times).

Here, since the switching-on count is at or above the maximum repetition count register 714, the repetition count modifier 711 returns the repetition count to the minimum repetition count (100 times) set in the minimum repetition count register 712, and awaits the next measurement timing with the non-invasive blood glucose measurement apparatus 101 (at 6 minutes).

Here, the switch-on timing 82 was changed from the minimum repetition count (100 times) to the maximum repetition count (300 times) according to the register group provided to the luminous energy level modifier 281 (the minimum repetition count register 712, the increased repetition count register 713, and the maximum repetition count register 714), but the repetition count may instead be changed by providing a register group that sets a plurality of repetition counts.

At a time of 6 minutes, measurement with the non-invasive blood glucose measurement apparatus 101 is performed at 6-minute intervals, so just as at a time of 0 minutes, the series of operations is performed for switching on the light source 201 at 100-time intervals from 100 to 300 times, and storing a characteristic quantity 61.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 12 minutes).

At a time of 10 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 82 mg/dL.

The user inputs to the non-invasive blood glucose measurement apparatus 101 the blood glucose measurement information 91 measured with the invasive blood glucose measurement apparatus (at a time of 10 minutes: 82 mg/dL).

The inputted blood glucose measurement information 91 is stored in the memory 205, inputted to the blood glucose level estimator 207, and compared with the blood glucose level at a time of 0 minutes (70 mg/dL), and a change of 12 mg/dL is calculated. Since the calculated change is less than the threshold of 70 mg/dL set in the calibration-use blood glucose threshold register 275, measurement with the invasive blood glucose measurement apparatus is continued.

At a time of 12 minutes, just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 18 minutes).

At a time of 18 minutes, just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 24 minutes).

At a time of 20 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 100 mg/dL.

The user inputs to the non-invasive blood glucose measurement apparatus 101 the blood glucose measurement information 91 measured with the invasive blood glucose measurement apparatus (at a time of 20 minutes: 100 mg/dL).

The inputted blood glucose measurement information 91 is stored in the memory 205, inputted to the blood glucose level estimator 207, and compared with the blood glucose level at a time of 0 minutes (70 mg/dL), and a change of 30 mg/dL is calculated. Since the calculated change is less than the threshold of 70 mg/dL set in the calibration-use blood glucose threshold register 275, measurement with the invasive blood glucose measurement apparatus is continued.

At a time of 24 minutes, just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 30 minutes).

At a time of 30 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 118 mg/dL.

The user inputs to the non-invasive blood glucose measurement apparatus 101 the blood glucose measurement information 91 measured with the invasive blood glucose measurement apparatus (at a time of 30 minutes: 118 mg/dL).

The inputted blood glucose measurement information 91 is stored in the memory 205, inputted to the blood glucose level estimator 207, and compared with the blood glucose level at a time of 0 minutes (70 mg/dL), and a change of 48 mg/dL is calculated. Since the calculated change is less than the threshold of 70 mg/dL set in the calibration-use blood glucose threshold register 275, measurement with the invasive blood glucose measurement apparatus is continued.

Just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 36 minutes).

At a time of 36 minutes, just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 42 minutes).

At a time of 40 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 125 mg/dL.

The user inputs to the non-invasive blood glucose measurement apparatus 101 the blood glucose measurement information 91 measured with the invasive blood glucose measurement apparatus (at a time of 40 minutes: 125 mg/dL).

The inputted blood glucose measurement information 91 is stored in the memory 205, inputted to the blood glucose level estimator 207, and compared with the blood glucose level at a time of 0 minutes (70 mg/dL), and a change of 60 mg/dL is calculated. Since the calculated change is less than the threshold of 70 mg/dL set in the calibration-use blood glucose threshold register 275, measurement with the invasive blood glucose measurement apparatus is continued.

At a time of 42 minutes, just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 48 minutes).

At a time of 48 minutes, just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 54 minutes).

At a time of 50 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 138 mg/dL.

The user inputs to the non-invasive blood glucose measurement apparatus 101 the blood glucose measurement information 91 measured with the invasive blood glucose measurement apparatus (at a time of 50 minutes: 138 mg/dL).

The inputted blood glucose measurement information 91 is stored in the memory 205, inputted to the blood glucose level estimator 207, and compared with the blood glucose level at a time of 0 minutes (70 mg/dL), and a change of 68 mg/dL is calculated. Since the calculated change is less than the threshold of 70 mg/dL set in the calibration-use blood glucose threshold register 275, measurement with the invasive blood glucose measurement apparatus is continued.

At a time of 54 minutes, just as at a time of 6 minutes, the non-invasive blood glucose measurement apparatus 101 performs the series of operations in which the light source 201 is switched on at 100-time intervals from 100 to 300 times, and a characteristic quantity 61 is stored.

When measurement is concluded at a repetition count of 300 times, the repetition count modifier 711 returns the repetition count to the minimum repetition count (100 times) set in the minimum repetition count register 712, and awaits the next measurement timing with the non-invasive blood glucose measurement apparatus 101 (at 60 minutes).

At a time of 60 minutes, just as at a time of 0 minutes, the user presses the blood sampling switch provided to the invasive blood glucose measurement apparatus, whereupon measurement is commenced by the invasive blood glucose measurement apparatus. The measurement method is the same as that at a time of 0 minutes.

Let us say that the blood glucose level at this point is 142 mg/dL.

The user inputs to the non-invasive blood glucose measurement apparatus 101 the blood glucose measurement information 91 measured with the invasive blood glucose measurement apparatus (at a time of 60 minutes: 142 mg/dL).

The inputted blood glucose measurement information 91 is stored in the memory 205, inputted to the blood glucose level estimator 207, and compared with the blood glucose level at a time of 0 minutes (70 mg/dL), and a change of 72 mg/dL is calculated. Since the calculated change is greater than the threshold of 70 mg/dL set in the calibration-use blood glucose threshold register 275, an approximation formula is calculated on the basis of the seven pieces of data for the invasive blood glucose measurement apparatus measured up to this point (70 mg/dL at a time of 0 minutes, 82 mg/dL at a time of 10 minutes, 100 mg/dL at a time of 20 minutes, 118 mg/dL at a time of 30 minutes, 125 mg/dL at a time of 40 minutes, 138 mg/dL at a time of 50 minutes, and 142 mg/dL at a time of 60 minutes), and the approximation curve 402 is found from the approximation formula thus calculated. Also, the approximated blood glucose levels at the timings measured with the non-invasive blood glucose measurement apparatus 101 are calculated from the approximation curve 402, and calibration data is calculated for each repetition count on the basis of the characteristic quantity 61 of the non-invasive blood glucose measurement apparatus 101 with respect to each repetition count, and these approximated blood glucose levels.

The estimated blood glucose level 72 for each repetition count is found from a time of 0 minutes until a time of 60 minutes on the basis of the calibration data thus calculated.

When the estimated blood glucose level 72 at each measurement time is calculated on the basis of the calibration data, we obtain the following.

At a time of 0 minutes:
the estimated blood glucose level 72 at a repetition count of 100 times is 68 mg/dL,
the estimated blood glucose level 72 at a repetition count of 200 times is 70 mg/dL, and
the estimated blood glucose level 72 at a repetition count of 300 times is 72 mg/dL.

At a time of 6 minutes:
the estimated blood glucose level 72 at a repetition count of 100 times is 75 mg/dL,
the estimated blood glucose level 72 at a repetition count of 200 times is 78 mg/dL, and
the estimated blood glucose level 72 at a repetition count of 300 times is 78 mg/dL.

At a time of 12 minutes:
the estimated blood glucose level 72 at a repetition count of 100 times is 82 mg/dL,
the estimated blood glucose level 72 at a repetition count of 200 times is 84 mg/dL, and
the estimated blood glucose level 72 at a repetition count of 300 times is 87 mg/dL.

At a time of 18 minutes:
the estimated blood glucose level 72 at a repetition count of 100 times is 84 mg/dL,
the estimated blood glucose level 72 at a repetition count of 200 times is 90 mg/dL, and
the estimated blood glucose level 72 at a repetition count of 300 times is 94 mg/dL.

At a time of 24 minutes:
the estimated blood glucose level 72 at a repetition count of 100 times is 87 mg/dL,
the estimated blood glucose level 72 at a repetition count of 200 times is 98 mg/dL, and
the estimated blood glucose level 72 at a repetition count of 300 times is 108 mg/dL.

At a time of 30 minutes:
the estimated blood glucose level 72 at a repetition count of 100 times is 95 mg/dL,
the estimated blood glucose level 72 at a repetition count of 200 times is 110 mg/dL, and
the estimated blood glucose level 72 at a repetition count of 300 times is 115 mg/dL.

At a time of 36 minutes:
the estimated blood glucose level 72 at a repetition count of 100 times is 100 mg/dL,
the estimated blood glucose level 72 at a repetition count of 200 times is 112 mg/dL, and
the estimated blood glucose level 72 at a repetition count of 300 times is 119 mg/dL.

At a time of 42 minutes:
the estimated blood glucose level 72 at a repetition count of 100 times is 101 mg/dL,
the estimated blood glucose level 72 at a repetition count of 200 times is 120 mg/dL, and
the estimated blood glucose level 72 at a repetition count of 300 times is 129 mg/dL.

At a time of 48 minutes:
the estimated blood glucose level 72 at a repetition count of 100 times is 102 mg/dL,
the estimated blood glucose level 72 at a repetition count of 200 times is 125 mg/dL, and
the estimated blood glucose level 72 at a repetition count of 300 times is 134 mg/dL.

At a time of 54 minutes:
the estimated blood glucose level 72 at a repetition count of 100 times is 102 mg/dL,
the estimated blood glucose level 72 at a repetition count of 200 times is 134 mg/dL, and
the estimated blood glucose level 72 at a repetition count of 300 times is 138 mg/dL.

At a time of 60 minutes:
the estimated blood glucose level 72 at a repetition count of 100 times is 103 mg/dL,
the estimated blood glucose level 72 at a repetition count of 200 times is 138 mg/dL, and
the estimated blood glucose level 72 at a repetition count of 300 times is 142 mg/dL.

Next, the repetition count selector 611 calculates the error by comparing the estimated blood glucose levels 72 from the non-invasive blood glucose measurement apparatus for each repetition count from a time of 0 minutes until a time of 60 minutes, with the blood glucose levels from the invasive blood glucose measurement apparatus or, when no blood glucose levels have been measured, the approximated blood glucose levels.

When the error is calculated at each measurement time, we obtain the following.

At a time of 0 minutes, the blood glucose level from the invasive blood glucose measurement apparatus is 70 mg/dL, so
the error from the estimated blood glucose level 72 at a repetition count of 100 times is 2 mg/dL,
the error from the estimated blood glucose level 72 at a repetition count of 200 times is 0 mg/dL, and
the error from the estimated blood glucose level 72 at a repetition count of 300 times is 0 mg/dL.

At a time of 6 minutes, the approximated blood glucose level from the invasive blood glucose measurement apparatus is 78 mg/dL, so the error from the estimated blood glucose level 72 at a repetition count of 100 times is 3 mg/dL, the error from the estimated blood glucose level 72 at a repetition count of 200 times is 0 mg/dL, and the error from the estimated blood glucose level 72 at a repetition count of 300 times is 0 mg/dL.

At a time of 12 minutes, the approximated blood glucose level from the invasive blood glucose measurement apparatus is 89 mg/dL, so the error from the estimated blood glucose level 72 at a repetition count of 100 times is 7 mg/dL, the error from the estimated blood glucose level 72 at a repetition count of 200 times is 5 mg/dL, and the error from the estimated blood glucose level 72 at a repetition count of 300 times is 2 mg/dL.

At a time of 18 minutes, the approximated blood glucose level from the invasive blood glucose measurement apparatus is 98 mg/dL, so the error from the estimated blood glucose level 72 at a repetition count of 100 times is 14 mg/dL, the error from the estimated blood glucose level 72 at a repetition count of 200 times is 8 mg/dL, and the error from the estimated blood glucose level 72 at a repetition count of 300 times is 4 mg/dL.

At a time of 24 minutes, the approximated blood glucose level from the invasive blood glucose measurement apparatus is 107 mg/dL, so the error from the estimated blood glucose level 72 at a repetition count of 100 times is 20 mg/dL, the error from the estimated blood glucose level 72 at a repetition count of 200 times is 9 mg/dL, and the error from the estimated blood glucose level 72 at a repetition count of 300 times is 1 mg/dL.

At a time of 30 minutes, the approximated blood glucose level from the invasive blood glucose measurement apparatus is 118 mg/dL, so the error from the estimated blood glucose level 72 at a repetition count of 100 times is 23 mg/dL, the error from the estimated blood glucose level 72 at a repetition count of 200 times is 8 mg/dL, and the error from the estimated blood glucose level 72 at a repetition count of 300 times is 3 mg/dL.

At a time of 36 minutes, the approximated blood glucose level from the invasive blood glucose measurement apparatus is 122 mg/dL, so the error from the estimated blood glucose level 72 at a repetition count of 100 times is 22 mg/dL, the error from the estimated blood glucose level 72 at a repetition count of 200 times is 10 mg/dL, and the error from the estimated blood glucose level 72 at a repetition count of 300 times is 3 mg/dL.

At a time of 42 minutes, the approximated blood glucose level from the invasive blood glucose measurement apparatus is 128 mg/dL, so the error from the estimated blood glucose level 72 at a repetition count of 100 times is 27 mg/dL, the error from the estimated blood glucose level 72 at a repetition count of 200 times is 8 mg/dL, and the error from the estimated blood glucose level 72 at a repetition count of 300 times is 1 mg/dL.

At a time of 48 minutes, the approximated blood glucose level from the invasive blood glucose measurement apparatus is 133 mg/dL, so the error from the estimated blood glucose level 72 at a repetition count of 100 times is 31 mg/dL, the error from the estimated blood glucose level 72 at a repetition count of 200 times is 8 mg/dL, and the error from the estimated blood glucose level 72 at a repetition count of 300 times is 1 mg/dL.

At a time of 54 minutes, the approximated blood glucose level from the invasive blood glucose measurement apparatus is 138 mg/dL, so the error from the estimated blood glucose level 72 at a repetition count of 100 times is 36 mg/dL, the error from the estimated blood glucose level 72 at a repetition count of 200 times is 4 mg/dL, and the error from the estimated blood glucose level 72 at a repetition count of 300 times is 0 mg/dL.

At a time of 60 minutes, the approximated blood glucose level from the invasive blood glucose measurement apparatus is 142 mg/dL, so the error from the estimated blood glucose level 72 at a repetition count of 100 times is 39 mg/dL, the error from the estimated blood glucose level 72 at a repetition count of 200 times is 4 mg/dL, and the error from the estimated blood glucose level 72 at a repetition count of 300 times is 0 mg/dL.

Next, the repetition count selector 611 calculates the average error for each repetition count, and outputs the smallest repetition count at which the calculated average error is under the preset estimated error register B 612, as the repetition count command signal 615.

The average error for each repetition count is:

20 mg/dL at a repetition count of 100 times, 5.8 mg/dL at a repetition count of 200 times, and 1.4 mg/dL at a repetition count of 300 times.

The repetition count selector 611 outputs a repetition count of 200 times, which is the smallest calculated average error that is under the average threshold for error preset in the estimated error register B 612 (10 mg/dL), as the repetition count command signal 615, and outputs the estimated blood glucose level 72 to the outside.

When the repetition count command signal 615 outputted from the blood glucose level estimator 207 is inputted to the controller 208, the repetition count modifier 711 changes the repetition count used for the normal measurement period to 200 times according to the repetition count command signal 615.

The periodic repetition count checker 715 begins measurement of elapsed time when the repetition count command signal 615 is detected.

In the description here, the calculated calibration data is used to calculate the estimated blood glucose level 72 from a time of 0 minutes up to a time of 60 minutes, the average error between the blood glucose levels from the invasive blood glucose measurement apparatus and the estimated blood glucose levels 72 at the various measurement times is found, and the repetition count used in the normal measurement period is determined, but another method may be used instead, such as determining the repetition count used in the normal measurement period by finding the error at the timing at which the calibration data is calculated, or determining the repetition count used in the normal measurement period by using the results during the calibration period.

When the calibration period is complete, the normal measurement period begins, and from a time of 66 minutes onward, measurement is performed with the non-invasive blood glucose measurement apparatus every six minutes.

At a time of 66 minutes, the elapsed time is 6 times.

Since the elapsed time does not exceed the 30 minutes preset in the checking cycle register B 716, the controller 208 controls the switch-on timing 82 at the repetition count (200 times) determined in the calibration period, the light source 201 is switched on, the characteristic quantity 61 of body information is calculated from the photoacoustic wave signal 105 generated by the light 103 from substances in the vein 104 that allow the blood glucose level to be estimated, and the estimated blood glucose level 72 based on the calibration data is found from the characteristic quantity 61 calculated by the blood glucose level estimator 207. The series of processing involving output to the outside is the same as in the calibration period.

From a time of 72 minutes onward, measurement is performed every six minutes with the non-invasive blood glucose measurement apparatus in the same manner as at an elapsed time of 66 minutes until the elapsed time exceeds 30 minutes.

At a time of 96 minutes, the elapsed time is 36 times.

Since the elapsed time exceeds the 30 minutes preset in the checking cycle register A 286, the controller 208 calculates the estimated blood glucose level 72 at the switch-on timing 82 for the repetition count determined in the calibration period (200 times), after which the periodic repetition count checker 715 continues to switch on the light source 201 until reaching the repetition count of 300 times preset in the checked luminous energy level register 287, and also performs measurement of the estimated blood glucose level 72 at a repetition count of 300 times.

First, the controller 208 controls the luminous energy level 81 and the switch-on timing 82 for a repetition count of 200 times to switch on the light source 201, calculates the characteristic quantity 61 of body information from the photoacoustic wave signal 105 generated by the light 103 from substances in the vein 104 that allow the blood glucose level to be estimated, and finds the estimated blood glucose level 72 based on the calibration data from the characteristic quantity 61 calculated by the blood glucose level estimator 207. Let us say that the estimated blood glucose level 72 at a repetition count of 200 times here is 162 mg/dL.

Next, the periodic repetition count checker 715 continues to switch on the light source 201 until reaching the repetition count of 300 times preset in the checked repetition count register 717, and when the repetition count reaches 300 times, the elapsed time that has been counted up to this point is reset, and measurement of the elapsed time is started over. The characteristic quantity 61 of body information is calculated from the photoacoustic wave signal 105 generated by the light 103 from the light source 201 from substances in the vein 104 that allow the blood glucose level to be estimated, and the estimated blood glucose level 72 based on the calibration data for a repetition count of 300 times calculated during the calibration period is found from the characteristic quantity 61 calculated by the blood glucose level estimator 207. Let us say that the estimated blood glucose level 72 at a repetition count of 300 times here is 163 mg/dL.

The favorable repetition count checker 613 provided to the blood glucose level estimator 207 calculates the error (1 mg/dL) by comparing the estimated blood glucose level (162 mg/dL) at a repetition count of 200 times with the estimated blood glucose level (163 mg/dL) at a repetition count of 300 times, and determines whether or not this error is at or under the 3 mg/dL preset in the favorable error register B 614. Since the error is under the preset favorable error register B 614, the repetition count restoration signal 616 is outputted to the controller 208 so as to return to the repetition count of 200 times set before being changed by the periodic repetition count checker 715. If the determination made by the favorable repetition count checker 613 is that the error is greater than the favorable error register B 614 that was preset, the repetition count restoration signal 616 is not outputted.

When the controller 208 detects the repetition count restoration signal 616 outputted from the blood glucose level estimator 207, the repetition count modifier 711 returns the repetition count to 200 times according to the repetition count restoration signal 616. If no repetition count restoration signal 616 can be detected, subsequent measurement is performed at the repetition count changed by the periodic repetition count checker 715 (the 300 times preset in the checked repetition count register 717).

Every six minutes from a time of 102 minutes onward, just as at a time of 66 minutes, measurement of the estimated blood glucose level 72 is performed at a repetition count of 200 times until the elapsed time exceeds the 30 minutes preset in the checking cycle register B 716.

Thus, with the non-invasive body information measurement apparatus pertaining to Embodiment 2 of the present invention, measurement with the non-invasive blood glucose measurement apparatus 101 in the calibration period is performed at a plurality of repetition counts, a plurality of estimated blood glucose levels are calculated from the plurality of characteristic quantities calculated at the various repetition counts and from the blood glucose levels measured with an invasive blood glucose measurement apparatus, upon completion of the calibration period the plurality of estimated blood glucose levels are compared with the blood glucose levels measured with the invasive blood glucose measurement apparatus, and measurement is performed in the normal measurement period at the smallest repetition count at which the calculated average error is under a preset threshold, so power consumption can be reduced and the measurement time can be shortened without diminishing the accuracy of the non-invasive blood glucose measurement apparatus, and the continuous measurement time can be greatly extended when the apparatus is used as a portable device.

Also, in Embodiment 2 of the present invention, it was explained that measurement in the normal measurement period was performed at the smallest repetition count at which the average error calculated by comparing a plurality of estimated blood glucose levels with the blood glucose levels measured with an invasive blood glucose measurement apparatus and calculated upon completion of the calibration period, that was under a preset threshold, but instead an approximation curve may be found for the average error for each repetition count, the repetition count that is under the threshold newly calculated, and the repetition count to be used in the normal measurement period calculated. Here again the same effect as above will be obtained.

Also, in Embodiment 2 of the present invention, the non-invasive blood glucose measurement apparatus 101 was assumed to be an apparatus that made use of photoacoustics, but may instead be another apparatus for finding blood glucose levels non-invasively. Here again the same effect as above will be obtained.

INDUSTRIAL APPLICABILITY

As discussed above, with the non-invasive body information measurement apparatus pertaining to the present invention, the luminous energy level or repetition count used in the normal measurement period is determined by comparing the estimated blood glucose level calculated during the calibration period with the blood glucose level measured with an invasive blood glucose measurement apparatus, which means that a non-invasive body information measurement apparatus that consumes less power and can measure in a shorter time can be provided, which is useful in improving the continuous measurement time of a portable device.

What is claimed is:

1. A non-invasive body information measurement apparatus comprising:
   a light source;
   a body information sensor that measures body information;
   a characteristic quantity detector that analyzes the body information measured by the body information sensor and calculates a characteristic quantity for the body information;
   a blood glucose level estimator that finds an estimated blood glucose level from the characteristic quantity calculated by the characteristic quantity detector and a measured blood glucose level measured by an invasive blood glucose measurement apparatus; and
   a controller that (i) during a calibration period performs measurement of the body information at a plurality of luminous energy levels and calculates a plurality of the estimated blood glucose levels from (a) a plurality of the characteristic quantities calculated at various luminous energy levels of the plurality of luminous energy levels and (b) the measured blood glucose levels measured by the invasive blood glucose measurement apparatus, (ii) at an end of the calibration period compares the plurality of the estimated blood glucose levels with the measured blood glucose levels measured by the invasive blood glucose measurement apparatus, and (iii) during a normal measurement period controls the light source so that measurement is performed at the plurality of luminous energy levels corresponding to the estimated blood glucose levels that satisfy a targeted accuracy,
   wherein the controller includes a luminous energy level modifier that controls a luminous energy level of the plurality of luminous energy levels according to a luminous energy level command signal outputted from the blood glucose level estimator.

2. The non-invasive body information measurement apparatus according to claim 1, wherein the blood glucose level estimator includes a luminous energy level selector that compares the plurality of the estimated blood glucose levels with the measured blood glucose levels measured by the invasive blood glucose measurement apparatus, calculates an average error, and detects a smallest luminous energy level at which the average error is under a preset threshold.

3. The non-invasive body information measurement apparatus according to claim 2,
   wherein the luminous energy level selector includes a register that can be written to from outside the luminous energy level selector, and
   wherein the luminous energy level selector changes the preset threshold based on a value of the register.

4. The non-invasive body information measurement apparatus according to claim 1,
   wherein the luminous energy level modifier includes a first register group that can be written to from outside the luminous energy level modifier, and
   wherein the luminous energy level modifier modifies the luminous energy level according to the luminous energy level command signal.

5. The non-invasive body information measurement apparatus according to claim 1, wherein the controller includes a periodic luminous energy level checker that, during the normal measurement period, changes a timing at which the light source is turned on in a preset cycle, and outputs the luminous energy level after changing the luminous energy level to a preset value.

6. The non-invasive body information measurement apparatus according to claim 5,
   wherein the periodic luminous energy level checker includes a register that can be written to from outside the periodic luminous energy level checker, and
   wherein the periodic luminous energy level checker changes the preset cycle based on a value of the register.

7. The non-invasive body information measurement apparatus according to claim 5,
   wherein the periodic luminous energy level checker includes a register that can be written to from outside the periodic luminous energy level checker, and
   wherein the periodic luminous energy level checker changes the luminous energy level based on a value of the register.

8. The non-invasive body information measurement apparatus according to claim 5, wherein the blood glucose level estimator includes a favorable luminous energy level checker that (i) compares the estimated blood glucose level measured at the luminous energy level changed by the periodic luminous energy level checker with the estimated blood glucose level measured at the luminous energy level set prior to being changed by the periodic luminous energy level checker, (ii) calculates an error, (iii) determines whether or not the error is at or below a preset threshold, and (iv), if the error is at or below the preset threshold, outputs to the controller a luminous energy level restoration signal so as to return to the luminous energy level set prior to being changed by the periodic luminous energy level checker.

9. The non-invasive body information measurement apparatus according to claim 8,
   wherein the favorable luminous energy level checker includes a register that can be written to from outside the favorable luminous energy level checker, and
   wherein the favorable luminous energy level checker changes the preset threshold based on a value of the register.

* * * * *